(12) United States Patent
Kim et al.

(10) Patent No.: US 9,874,501 B2
(45) Date of Patent: Jan. 23, 2018

(54) USE OF CHEMICALLY PATTERNED SUBSTRATE FOR LIQUID HANDLING, CHEMICAL AND BIOLOGICAL REACTIONS

(71) Applicant: Curiox Biosystems Pte Ltd., Singapore (SG)

(72) Inventors: Namyong Kim, Palo Alto, CA (US); Li Li, Singapore (SG)

(73) Assignee: Curiox Biosystems Pte Ltd., Singapore (SG)

( * ) Notice: Subject to any disclaimer, the term of this patent is extended or adjusted under 35 U.S.C. 154(b) by 0 days.

(21) Appl. No.: 14/338,168

(22) Filed: Jul. 22, 2014

(65) Prior Publication Data

US 2014/0338702 A1 Nov. 20, 2014

Related U.S. Application Data

(63) Continuation-in-part of application No. 13/264,913, filed as application No. PCT/SG2010/000153 on Apr.
(Continued)

(51) Int. Cl.
*B01L 99/00* (2010.01)
*G01N 1/34* (2006.01)
(Continued)

(52) U.S. Cl.
CPC ............. *G01N 1/34* (2013.01); *B01L 3/5085* (2013.01); *B01L 3/5088* (2013.01); *B01L 9/523* (2013.01);
(Continued)

(58) Field of Classification Search
None
See application file for complete search history.

(56) References Cited

U.S. PATENT DOCUMENTS 3,426,108 A 2/1969 Britten
3,754,872 A 8/1973 Zauft
(Continued)

FOREIGN PATENT DOCUMENTS

CN 1460723 A 12/2003
CN 1858593 A 11/2006
(Continued)

OTHER PUBLICATIONS

Agency for Science, Technology and Research, Communication Pursuant to Article 94, EP07835548-4, Jul. 17, 2015, 3 pgs.
(Continued)

*Primary Examiner* — Jill Warden
*Assistant Examiner* — Julie Tavares
(74) *Attorney, Agent, or Firm* — Morgan, Lewis & Bockius LLP

(57) ABSTRACT

A device for washing an array plate having an array of liquid droplets adhered thereto is described. The array of liquid droplets is covered with a hydrophobic medium immiscible with the array of liquid droplets. The device includes a mechanism for draining the hydrophobic medium from the array plate; a mechanism for providing an aqueous wash liquid over the array plate; a mechanism for shaking the array plate in a presence of the aqueous wash liquid; and a mechanism for removing the aqueous wash liquid from the array plate. A method for washing an array plate is also described.

23 Claims, 18 Drawing Sheets

Related U.S. Application Data 16, 2010, now Pat. No. 8,784,752, application No. 14/338,168, filed on Jul. 22, 2014, which is a continuation-in-part of application No. 14/246,004, filed on Apr. 4, 2014, which is a continuation of application No. 11/984,197, filed on Nov. 14, 2007, now Pat. No. 8,691,147, which is a continuation-in-part of application No. PCT/SG2006/000363, filed on Nov. 24, 2006.

(60) Provisional application No. 61/170,201, filed on Apr. 17, 2009.

(51) Int. Cl.
| | |
|---|---|
| G01N 1/38 | (2006.01) |
| G01N 35/02 | (2006.01) |
| B01L 3/00 | (2006.01) |
| B01L 9/00 | (2006.01) |
| B08B 3/10 | (2006.01) |

(52) U.S. Cl.
CPC ............ *B08B 3/10* (2013.01); *G01N 1/38* (2013.01); *G01N 35/028* (2013.01); *B01L 2200/026* (2013.01); *B01L 2300/022* (2013.01); *B01L 2300/0822* (2013.01); *B01L 2300/0829* (2013.01); *B01L 2400/0457* (2013.01)

(56) References Cited

U.S. PATENT DOCUMENTS

| | | | |
|---|---|---|---|
| 5,041,266 A | 8/1991 | Fox | |
| 5,219,528 A | 6/1993 | Clark | |
| 5,229,163 A | 7/1993 | Fox | |
| 5,506,121 A | 4/1996 | Skena et al. | |
| 5,560,811 A | 10/1996 | Briggs et al. | |
| 5,691,147 A | 11/1997 | Draetta | |
| RE35,894 E | 9/1998 | Ellison et al. | |
| 5,817,510 A | 10/1998 | Pandey et al. | |
| 6,048,908 A | 4/2000 | Kitagawa | |
| 6,086,825 A | 7/2000 | Sundberg et al. | |
| 6,103,493 A | 8/2000 | Skerra et al. | |
| 6,130,098 A | 10/2000 | Handique et al. | |
| 6,238,626 B1 | 5/2001 | Higuchi et al. | |
| 6,331,441 B1 | 12/2001 | Balch et al. | |
| 6,534,014 B1 | 3/2003 | Mainquist et al. | |
| 6,565,813 B1 | 5/2003 | Garyantes | |
| 6,578,952 B1 | 6/2003 | Sugiyama et al. | |
| 6,664,044 B1 | 12/2003 | Sato | |
| 6,699,437 B1 * | 3/2004 | Astle .............. | B01L 9/523 422/553 |
| 6,716,629 B2 | 4/2004 | Hess et al. | |
| 6,767,733 B1 | 7/2004 | Green | |
| 6,902,705 B1 | 6/2005 | Caillat et al. | |
| 7,163,823 B2 | 1/2007 | Patno et al. | |
| 7,344,877 B1 | 3/2008 | Camacho et al. | |
| 7,439,056 B2 | 10/2008 | Duffy et al. | |
| 7,666,362 B2 | 2/2010 | Shanler | |
| 7,794,799 B1 | 9/2010 | Kim et al. | |
| 7,854,343 B2 | 12/2010 | Ellson et al. | |
| 8,221,697 B2 | 7/2012 | Nichols et al. | |
| 8,337,778 B2 | 12/2012 | Stone et al. | |
| 8,987,174 B2 | 3/2015 | Routenberg | |
| 2002/0016009 A1 | 2/2002 | Ogura | |
| 2002/0064482 A1 | 5/2002 | Tisone et al. | |
| 2002/0094533 A1 | 7/2002 | Hess et al. | |
| 2003/0032046 A1 | 2/2003 | Duffy et al. | |
| 2003/0083474 A1 | 5/2003 | Schmidt | |
| 2003/0113813 A1 | 6/2003 | Heidaran et al. | |
| 2003/0124599 A1 | 7/2003 | Chen et al. | |
| 2003/0148401 A1 | 8/2003 | Agrawal et al. | |
| 2003/0209560 A1 | 11/2003 | Hui et al. | |
| 2004/0106156 A1 * | 6/2004 | Perez .............. | G01N 33/5008 435/7.2 |
| 2004/0106191 A1 | 6/2004 | Muser | |
| 2004/0136876 A1 | 7/2004 | Fouillet et al. | |
| 2004/0142460 A1 | 7/2004 | Cima et al. | |
| 2004/0208792 A1 | 10/2004 | Linton et al. | |
| 2004/0234966 A1 | 11/2004 | Bryning et al. | |
| 2005/0045539 A1 | 3/2005 | Yu et al. | |
| 2005/0079105 A1 | 4/2005 | Hunter et al. | |
| 2005/0084423 A1 * | 4/2005 | Zarowitz .............. | B01L 3/021 422/504 |
| 2005/0186579 A1 | 8/2005 | Dellinger et al. | |
| 2006/0013031 A1 | 1/2006 | Ravkin et al. | |
| 2006/0051249 A1 | 3/2006 | Knebel et al. | |
| 2006/0078893 A1 | 4/2006 | Griffiths et al. | |
| 2006/0105453 A1 | 5/2006 | Brenan et al. | |
| 2006/0105462 A1 | 5/2006 | Sellek-Prince | |
| 2006/0142468 A1 | 6/2006 | Downing, Jr. et al. | |
| 2007/0003448 A1 | 1/2007 | Kanigan et al. | |
| 2007/0005169 A1 * | 1/2007 | Rohnert .............. | G01N 1/31 700/100 |
| 2007/0077651 A1 | 4/2007 | Guarino et al. | |
| 2007/0099208 A1 | 5/2007 | Drmanac et al. | |
| 2007/0117765 A1 | 5/2007 | Sauve et al. | |
| 2008/0003671 A1 | 1/2008 | Martin | |
| 2008/0173544 A1 | 7/2008 | Seul et al. | |
| 2009/0142564 A1 | 6/2009 | Plissonnier et al. | |
| 2009/0148348 A1 | 6/2009 | Pettigrew et al. | |
| 2009/0227474 A1 | 9/2009 | Gordon et al. | |
| 2009/0286317 A1 | 11/2009 | Demmler et al. | |
| 2010/0000304 A1 | 1/2010 | Kim et al. | |
| 2010/0167950 A1 | 7/2010 | Juang et al. | |
| 2010/0297767 A1 | 11/2010 | Hattori et al. | |
| 2012/0220497 A1 | 8/2012 | Jacobson et al. | |

FOREIGN PATENT DOCUMENTS

| | | |
|---|---|---|
| CN | 101031363 A | 9/2007 |
| DE | 10043042 C2 | 6/2002 |
| EP | 0812693 A1 | 12/1997 |
| EP | 1348533 B1 | 7/2002 |
| EP | 1358939 A2 | 4/2003 |
| EP | 1316360 B1 | 6/2003 |
| EP | 1386657 A1 | 7/2003 |
| EP | 1473079 A1 | 2/2004 |
| EP | 1399263 B1 | 3/2004 |
| EP | 1788047 A1 | 8/2005 |
| EP | 1683571 A1 | 1/2006 |
| GB | 1291610 | 10/1972 |
| GB | 2332273 A | 6/1999 |
| GB | 2334954 A | 9/1999 |
| JP | 3120453 B2 | 12/2000 |
| JP | 2002-502955 A | 1/2002 |
| JP | 2003-033177 A | 2/2003 |
| JP | 2004-020280 A | 1/2004 |
| JP | 2004-077476 A | 3/2004 |
| JP | 2004-535176 A | 11/2004 |
| JP | 2005-003803 A | 1/2005 |
| JP | 2005-099004 A | 4/2005 |
| WO | WO 1996-23879 | 8/1996 |
| WO | WO 1998-055852 | 12/1998 |
| WO | WO 99/39829 A1 | 8/1999 |
| WO | WO 99/55826 | 11/1999 |
| WO | WO 2000-014311 | 3/2000 |
| WO | WO 00-58735 | 10/2000 |
| WO | WO 2001-004144 A2 | 1/2001 |
| WO | WO 2003-029462 A1 | 4/2003 |
| WO | WO 2004-030820 A2 | 4/2004 |
| WO | WO 2004-111610 A2 | 12/2004 |
| WO | WO 2005/019254 A1 | 3/2005 |
| WO | WO 2005/019255 A1 | 3/2005 |
| WO | WO 2005/019256 A2 | 3/2005 |
| WO | WO 2006/004739 A2 | 1/2006 |
| WO | WO 2006/046699 A1 | 5/2006 |
| WO | WO 2007/102785 A1 | 9/2007 |
| WO | WO 2008/063136 A1 | 5/2008 |
| WO | WO 98/47003 | 10/2008 |

(56) References Cited

FOREIGN PATENT DOCUMENTS

WO     WO 2010/120249 A1     10/2010
WO     WO 2012/011877 A2     1/2012

OTHER PUBLICATIONS

Kim, Office Action, U.S. Appl. No. 13/811,638, dated Sep. 11, 2015, 29 pgs.
Curiox Biosystems PTE Ltd., International Search Report and Written Opinion, PCT/U52015/019760, dated Jun. 2, 2015, 12 pgs.
Agency for Science, Technology and Research, Decision to Grant, JP2012-196318, dated Sep. 12, 2014, 3 pgs.
Curiox Biosystems Pte Ltd, International Preliminary Report on Patentablity, PCT/IB2013/000623, dated Aug. 5, 2014, 7 pgs.
Agency for Science, Technology and Research, Decision to Grant, Application No. CN201110401674.9, dated Aug. 7, 2014, 2 pgs.
Agency for Science, Technology and Research, International Preliminary Report on Patentability, PCT/SG2007/000393, dated May 26, 2009, 4 pgs.
Agency for Science, Technology and Research, International Search Report and Written Opinion of the ISA, PCT/SG2007/000393, dated Feb. 20, 2008, 7 pgs.
Agency for Science, Technology and Research, Notification of First Office Action, CN 201110401674.9, dated Dec. 30, 2013, 9 pgs.
Agency for Science, Technology and Research, Notification of Reasons for Refusal, JP 2009-538373, dated Nov. 11, 2011, 7 pgs.
Agency for Science, Technology and Research, Notification of Reasons for Refusal, JP 2012-196318, dated Dec. 10, 2013, 3 pgs.
Agency for Science, Technology and Research, Notification of the First Office Action, CN 200780048922.8, dated Nov. 12, 2010, 4 pgs (available in Chinese only).
Agency for Science, Technology and Research, Notification of the Second Office Action, CN 200780048922.8, dated May 17, 2011, 4 pgs.
Agency for Science, Technology and Research, Notification on the Grant of Patent Right for Invention, CN 200780048922.8, dated Sep. 22, 2011, 1 pg.
Agency for Science, Technology and Research, Supplementary Search Report, EP 07835548.4, dated Jun. 30, 2010, 5 pgs.
Asberg, Surgace Energy Modified Chips for Detection of Conformational States and Enzymatic Activity in Biomolecules, Langmuir, 2006, pp. 2205-2211.
Beck, Improving Stamps for 10 nm Level Wafer Scale Nanoimprint Lithography, Microelectron. Eng., 2002, pp. 61-62 and 441.
Benor, Microstructuring by Microcontact Printing and Selective Surface Dewetting, J. of Vacuum Science & Technology B, 2007, pp. 1321-1326.
Beste, Small Antibody-like Proteins with Prescrived Ligand Specificities Derived from the Lipocalin Fold, Proc. Natl. Acad. Sci, USA, 1999, pp. 1898-1903.
Biffinger, The Polar Hydrophobicity of Cluorinated Compounds, ChemBioChem, 2004, pp. 622-627.
Burbulis, Quantifying Small Numbers of Antibodies with a 'Near-Universal' Protein-DNA Chimera, Nature Methods, 2007.
Chiriac, Magnetic GMI Sensor for Detection of Biomolecules, J. Magnetism and Magnetic Materials, 2005, pp. 671-676.
Churaev, Wetting of Low-Energy Surgfaces, Advances in Colloid and Interface Science, 2007, pp. 134-135, 15-23.
Curiox Biosystems Pte Ltd, International Preliminary Report on Patentablity, PCT/SG2010/000153, dated Oct. 18, 2011, 15 pgs.
Curiox Biosystems Pte Ltd, International Preliminary Report on Patentability, PCT/SG2011/000263, dated Dec. 21, 2012, 7 pgs.
Curiox Biosystems Pte Ltd, International Search Report and Written Opinion, PCT/IB2013/000623, dated Jul. 10, 2013, 7 pgs.
Curiox Biosystems Pte Ltd, International Search Report and Written Opinion, PCT/SG2006/000050, dated May 8, 2006, 21 pgs.
Curiox Biosystems Pte Ltd, International Search Report and Written Opinion, PCT/SG2010/000153, dated Sep. 17, 2010, 20 pgs.

Curiox Biosystems Pte Ltd, International Search Report and Written Opinion, PCT/SG2011/000263, dated Feb. 29, 2012, 20 pgs.
Daniel, Vibration-Actuated Drop Motion on Surfaces bor Batch Microfluidic Processes, Langmuir, 2005, pp. 4220-4228.
Dill, Modeling Water, The Hydrophobic Effect and Ion Solvation, Annu. Rev. Biophys. Biomol. Struc, 2005, pp. 173-199.
Gao, A Commercially Available Perfectly Hydrophobic Material, Langmuir, 2007, pp. 9125-9127.
Gascoyne, Dielectrophoresis-based Programmable Fluidic Processors, Lab-on-a-Chip, 2004, pp. 299-309.
Genua, Functional Patterns Obtained by Nanoimprinting Lithography and Subsequent Growth of Polymer Brushes, Nanotechnology, 2007, 215301, 7 pgs.
Gill, Pharmaceutical Drug Discovery Using Novel Protein Scaffolds, Current Opinion in Biotechnology, 2006, 653-658.
Giovambattista, Effect of Surface Polarity on Water Contact Angle and Interfacial Hydration Structure, J. Phys. Chem., 2007, pp. 9581-9587.
Goddard, Polymer Surface Modification for the Attachment of Bioactive Compounds, Progress in Polymer Science, 2007, pp. 698-725.
Griffiths, Miniaturising the Laboratory in Emulsion Droplets, Trends in Biotechnology, 2006, pp. 395-402.
Herrmann, Enxymatically-Generated Fluorescent Detection in Micro-Channels with Internal Magnetic Mixing for the Development of Parallel Miicrofluidic ELISA, Lab-on-a-Chip, 2006, pp. 555-560.
Holt, Domain Antibodies: Proteins for Therapy, Trends Biotechnol, 2003, pp. 484-490.
Hutten, New Magnetic Nanoparticles for Biotechnology, J. Biotech., 2004, pp. 47-63.
Iliades, Triabodics: Single Chain Fv Fragments without a Linker Form Trivalent Trimers, FEBS Lett, 1997, pp. 437-441.
Jakobs, Micrometer Scale Gel Patterns, Colloids & Surfaces A: PhysioChem. Eng. Aspects, 2006, pp. 33-40.
Jung, Wetting Transition of Water Droplets on Superhydrophobic Patterned Surfaces, Scripta Materialia, 2007, pp. 1057-1060.
Kanta, Preparation of Silica-on-Titania Patterns with a Wettability Contrast, Langmuir, 2005, 5790-5794.
Kim, Final Office Action, U.S. Appl. No. 13/264,913, dated Jun. 21, 2013, 11 pgs.
Kim, Notice of Allowance, U.S. Appl. No. 12/282,162, dated May 14, 2012, 7 pgs.
Kim, Office Action, U.S. Appl. No. 12/282,162, dated Jun. 27, 2011, 8 pgs.
Kim, Office Action, U.S. Appl. No. 13/264,913, dated Nov. 7, 2012, 9 pgs.
Kim, Office Action, U.S. Appl. No. 13/264,913, dated Sep. 26, 2013, 10 pgs.
Kusumaatmaja, Controlling Drop Size and Polydispersity Using Chemically Patterned Surfaces, Langmuir, 2007, pp. 956-959.
Kwon, Quantitative Evaluation of the Relative Cell Permeability of Peptoids and Peptides, J. Am. Chem. Soc., 2007, pp. 1508-1509.
Leck, Final Office Action, U.S. Appl. No. 11/984,197, dated May 8, 2012, 10 pgs.
Leck, Office Action, U.S. Appl. No. 11/984,197, dated Mar. 14, 2013, 11 pgs.
Leck, Office Action, U.S. Appl. No. 11/984,197, dated May 26, 2011, 11 pgs.
Leck, Office Action, U.S. Appl. No. 11/984,197, dated Jul. 31, 2013, 12 pgs.
Li, What Do We Need for a Superhydrophobic surface? A review on the recent progress in the preparation of superhydrophobic surfaces, Chem. Soc. Rev, 2007, pp. 1350-1368.
Luca, Preparation of TIOx Thin Films by Reactive Pulsed-Laser Ablation, J. Optoelectronics and Adv. Materials, Apr. 2005, pp. 625-630.
Lundgren, Modeling of Wetting: A Study of Nanowetting at Rough and Heterogeneous Surfaces, Langmuir, 2007, pp. 1187-1194.
Ma, Superhydrophobic Surfaces, Current Opinion in Colloid & Interface Science, 2006, pp. 193-202.

(56) References Cited

OTHER PUBLICATIONS

Mardare, Microelectrochemical Lithography: A method for Direct Writing of Surface Oxides, Electrochimica Acta, 2007, pp. 7865-7869.
Matsuda, Phosphorylcholine-Endcapped Oligomer and Block Co-Oligomer and Surface Biological Reactivity, Biomaterials, 2003, pp. 4517-4527.
Meyer, Recent Progress in Understanding Hydrophobic Interactions, Proc. Netl. Acad. Sci USA, 2006, pp. 15739-15746.
Mosavi, The Ankyrin Repeat as Molecular Architecture for Protein Recognition, Protein Science, 2004, pp. 1435-1448.
Opdahl, Polymer Surface Science, The Chemical Record, 2001, pp. 101-122.
Perfulorodecalin-FluoroMed, http://fluoromed.com/products/perfluorodecalin.html (no date).
Pollack, Electrowetting-based Actuation of Liquid Droplets for Microfluidic Applications, Appl. Phys. Lett., 2000, pp. 1725-1726.
Popp, Sortagging: A versatile Method for Protein Labeling, Nature Chemical Biology, 2007, pp. 707-708.
Rastogi, Development and Evaluation of Realistic Microbioassys in Freely Suspended Droplets on a Chip, Biomicrofludics, 2007, 014107-1-014107-17.
Roach, Controllling Nonspecific Protein Adsorption in a Plug-Based Microfluidic System by Controlling Interfacial Chemistry Using Fluorous-Phase Surfactants, Analytical Chemistry, vol. 77, No. 3, Feb. 1, 2005, pp. 785-796.
Ronaghi, Pyrosequestering Sheds Light on DNA Sequestering, Genome Research, 2001, pp. 3-11.
Rose, Microdispensing Technologies in Drug Discovery, Drug Discovery Today, 1999, pp. 411-419.
Satriano, Bacterial Adhesion Onto Nanopatterned Polymer Surfaces, Materials Science & Engineering C, 2006, pp. 942-946.
Silverman, Multivalent Avimer Proteins Evolved by Exon Shuffling of a Family of Human Receptor Domains, Nature Biotechnology, 2005, pp. 1556-1561.
Skerra, Engineered Protein Scaffolds for Molecular Recognition, J. Mol. Recognit., 2000, pp. 167-187.
Song, Miniature Biochip System for Detection of Sscherichi coli O157:H7 Based on Antibody-Immobilized Capillary Reactors and Enzyme-linked Immunosorbent Assay, Analytica Chimica Acta, 2004, pp. 115-121.
Stephenson, Quantifying the Hydrophobic Effect: A Computer Simulation-Molecular-Thermodynamic Model for the Self-Assembly of Hydrophibic and Amphiphilic Solutes in Aqueous Solution, Jp. Phys. Chem. B, 2007, 1025-1044.
Stone, The Assembly of Single Domain Antibodies into Bispecific Decavalent Molecules, J. Immunological Methods, 2007, pp. 88-94.
Sundberg, Contact Angle Measurements by Confocal Microscopy for Non-Destructive Microscale Surface Characterization, J. Colloid and Interface Science, 2007, pp. 454-460.
Van Oss, Long-Rage and Short-Range Mechanisms of Hydrophobic Attraction and Hydrophilic Repulsion in Specific and Aspecific Interactions, J. Mol. Recognit., 2003, pp. 177-190.
Wang, Flow-Focusing Generation of Monodisperse Water Droplets Wrapped by Ionic Liquid on Microfluidic Chips: From Plug to Sphere, langmuir, 2007, pp. 11924-11931.
Wang, In-Situ Wilhelmy Balance Surface Energy Determination of Poly(3-hexylthiophere) and Poly(3,4-ethylenedioxythiophere) during Electrochemical Doping-Dedoping, Langmuir, 2006, pp. 9287-9294.
Washizu, Elccrostatic Actuation of Liquid Droplets for Microreactor Applications, IEEE Transactions on Industry Applications, vol. 34, No. 4, Jul.-Aug. 1998.
West, Microplasma Writing for Surface-Directed Millifludics, Lab-on-a-Chip, 2007, pp. 981-983.
Widom, The Hydrophobic Effect, Phys. Chem. Chem. Phys., 2003, pp. 3085-3093.
Wixforth, Flatland Fluidics, mstnews, 2002, pp. 42-43.
Kim, Office Action, U.S. Appl. No. 14/326,780, dated Oct. 28, 2015, 13 pgs.
Kim, Office Action, U.S. Appl. No. 14/452,172, dated Oct. 23, 2015, 16 pgs.
Cheng, Office Action, U.S. Appl. No. 14/050,321, dated Feb. 26, 2016, 31 pgs.
Erfle et al., "Reverse Transfections on Cell Arrays for High Content Screening Microscopy," Nature Protocols, Mar. 1, 2007, vol. 2 No. 2, 8 pgs.
Kim, Final Office Action, U.S. Appl. No. 14/326,780, dated May 10, 2016, 11 pgs.
Lowe et al., "Perfluorochemicals: Their Applications and Benefits to Cell Culture," Tibtech, Jun. 1998, vol. 16, 6 pgs.
Takahashi et al., Induction of Pluripotent Stem Cells from Mouse Embryonic and Adult Fibroblast Cultures by Defined Factors, Cell, Aug. 25, 2006, 126, 14 pgs.
Vancha et al., "Use of Polyethyleneimine Polymer in Cell Culture as Attachment Factor and Lipofection Enhancer," BMC Biotechnology, Oct. 15, 2004, 12 pgs.
Agency for Science, Technology and Research, First Examination Report, IN3674/CHEN/P2009, dated Oct. 7, 2016, 9 pgs.
Kim, Notice of Allowance, U.S. Appl. No. 14/326,780, dated Sep. 22, 2016, 7 pgs.
Leck, Notice of Allowance, U.S. Appl. No. 14/246,004, dated Sep. 15, 2016, 8 pgs.
Kim, Final Office Action, U.S. Appl. No. 13/811,638, dated Apr. 21, 2016, 24 pgs.
Kim, Final Office Action, U.S. Appl. No. 14/452,172, dated Jun. 3, 2016, 17 pgs.
Cheng, Office Action, U.S. Appl. No. 14/050,321, dated Mar. 31, 2017, 38 pgs.
Kim, Final Office Action, U.S. Appl. No. 13/811,638, dated Feb. 9, 2017, 29 pgs.

* cited by examiner

Tilting Action at 0, 90 and 120 degree

Tilt at 0 degree for loading/unloading and washing

Tilt at 90 degree for addition of wash buffer

Tilt at 120 degree draining wash buffer and oil

USE OF CHEMICALLY PATTERNED SUBSTRATE FOR LIQUID HANDLING, CHEMICAL AND BIOLOGICAL REACTIONS

RELATED APPLICATIONS

This application is a continuation-in-part of U.S. patent application Ser. No. 13/264,913, filed Oct. 17, 2011, which is a national stage application of International Application Serial No. PCT/SG2010/000153, filed Apr. 16, 2010, which claims priority to U.S. Provisional Patent Application Ser. No. 61/170,201, filed Apr. 17, 2009. This application is a continuation-in-part of U.S. patent application Ser. No. 14/246,004, filed Apr. 4, 2014, which is a continuation application of U.S. patent application Ser. No. 11/984,197, filed Nov. 14, 2007, which is a continuation-in-part of International Application Serial No. PCT/SG2006/000363, filed Nov. 24, 2006. All of these applications are incorporated by reference herein in their entirety.

TECHNICAL FIELD

This application generally relates to systems and methods for handling small volumes of liquids and, more particularly, systems and methods for washing samples in small volumes of liquids on an array plate.

BACKGROUND

Biological, biochemical and chemical analyses are often performed in a microplate format. Standard format microplates are promulgated by the Society for Biomolecular Screening (SBS). Of these, 96-well, 384-well, and 1536-well microplates are commonly used in scientific, analytical, and diagnostic pursuits. The SBS format enjoys an ecosystem of instrumentation suppliers for automated liquid handling, incubation, plate reading, plate storage and plate handling.

An alternate microwell format is based on hydrophobic/hydrophilic patterning. Arrays with hydrophilic elements in a hydrophobic background are available commercially (e.g., PTFE printed slides from TEKDON, Myakka City, Fla., USA).

SUMMARY

In accordance with some embodiments, there is a holder for holding a liquid handling plate. The holder includes a generally rectangular frame sized to hold the plate and having a circumferential side wall. At least one portion of the side wall of the frame has a sloping feature having a slope such that when a plate is mounted in the frame to form a mounted structure and a liquid is held in the mounted structure so as to contact the frame in a draining position, gravity will cause the liquid to be drawn downward along the slope.

Some embodiments include additional or optional features. In some embodiments, an identification feature suitable for communication with an automated instrument for washing the mounted structure is usable to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, and/or to record the date of production of the plate, the date of expiry of the plate, or the number of times the plate has been washed. The identification feature is optionally a writable feature such as an RFID device operable to store information written by the machine such as an update to the number of times the plate has been washed.

Furthermore, in some embodiments, the holder may comprise a plurality of feet sized to elevate the plate by a fixed amount to thereby create a gap which enhances the parallel positioning of the plate relative to the holder when a sealant such as an adhesive or elastomer is positioned in the gap.

In some embodiments, the holder may also comprise a raised portion mounted atop the side wall for sealingly contacting a cover when pressed against a gasket, the raised portion preferably positioned near the inside edge of the side wall.

In accordance with some embodiments, there is a holder together with the plate, where the plate further comprising an array of hydrophilic regions in a hydrophobic background, the hydrophilic regions are preferably arranged with an industry standard microplate spacing, and the plate is preferably positioned with a flatness of less than 200 micrometers over the area of the plate.

In some embodiments, the holder further comprises at least one cutout positioned to mechanically signal information to an array of switches on a receiving platform of a corresponding plate washing instrument.

In accordance with some embodiments, there is a liquid handling plate that comprises an array of hydrophilic regions in a hydrophobic background. The hydrophilic regions are preferably arranged with an industry standard microplate spacing. The plate also includes an array holder for mounting the array and an identification feature suitable for communication with an automated instrument for washing the mounted structure to perform an assay.

In some embodiments, the identification feature carries information usable by a plate washing machine. The information can be usable by the plate washing machine to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, and/or to record the date of production of the plate, the date of expiry of the plate, or the number of times the plate has been washed. The identification feature is optionally a writable feature such as an RFID device operable to store information written by the machine such as an update to the number of times the plate has been washed.

In some embodiments, the plate comprises a raised portion atop the side wall for sealingly contacting a cover when pressed against a gasket, the raised portion preferably positioned near the inside edge of the side wall.

In some embodiments, the plate includes a support grid adapted to support the substrate in a generally planar position and preferably having openings aligned with the hydrophilic regions so as to permit optical interrogation thereof.

In some embodiments, there is a system, including the above-mentioned plate together with a plate washing machine operable to extract information from and optionally write information to the identification feature. The identification feature may comprise a cutout positioned for actuating an array of switches on a receiving platform of a plate washing machine.

In accordance with some embodiments, there is a fluid-exchange cover for sealingly coveting a fluidic plate. The cover includes a fluidic channel system comprising one or both of an oil inlet in fluid communication with an oil outlet and, optionally, an air vent, arranged so that when the cover is held sealingly against a fluidic plate having a wall, fluid injected into the inlet is directed against the wall in a manner that does not disrupt liquid adhered to hydrophilic regions of the plate; and a washing liquid inlet in communication with a branched channel structure that divides the flow of washing liquid injected into the channel so as to lessen a potential impact of the washing liquid against the hydrophilic elements.

In accordance with some embodiments, there is a method for controlling a residual volume of an aqueous solution bathing an array comprising a plurality of hydrophilic elements on a hydrophobic background. The method comprises adding an aqueous liquid so as to contact the hydrophilic elements, tilting the array to a selected angle from a horizontal reference plane (wherein the angle is less than 120 degrees and preferably between 5 degrees and 115 degrees, more preferably between 15 and 90 degrees), and allowing the aqueous liquid to drain while leaving a residual volume adhered to the elements.

In some embodiments, the method comprises selecting a desired residual volume and selecting a corresponding angle so as to leave behind the desired residual volume.

In accordance with some embodiments, there is a device for holding an array of liquid aqueous liquid droplets. The device comprises a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid. The hydrophobic liquid is immiscible with the aqueous liquid and, preferably, the surface tension of the hydrophobic liquid is equal to or greater than the surface tension of the hydrophobic background and the surface tension of the immiscible liquid is lower than that of the aqueous liquid.

In some embodiments, the aqueous liquid may be phosphate buffered saline. The immiscible liquid may have a kinematic viscosity of less than 20 cSt, and preferably less than 15 cSt. The layer of hydrophobic liquid may be less than 5 mm thick and preferably less than 1 mm thick. The immiscible liquid may comprises a perfluorocarbon, preferably having a vapor pressure low enough to allow use of the device without exposing the hydrophobic background for 2 or more hours. The device may be packaged to prevent gas exchange, preferably so as to maintain the immiscible liquid for 6-12 months or more. The device may have a roughened hydrophobic background, preferably characterized by an rms roughness of 50-100 micrometers or greater.

In accordance with some embodiments, there is a method for protecting an array of hydrophilic elements on a hydrophobic background from wetting by a hydrophobic liquid introduced to the array. The method includes selectively coating the hydrophobic background with a layer of hydrophobic liquid that imparts additional nonwetting characteristics to the hydrophobic background when challenged with an aqueous liquid. The hydrophobic liquid is immiscible with the aqueous liquid and, preferably, the surface tension of the hydrophobic liquid is equal to or greater than the surface tension of the hydrophobic background and the surface tension of the immiscible liquid is lower than that of the aqueous liquid.

In some embodiments, the aqueous liquid may be phosphate buffered saline. The immiscible liquid may have a kinematic viscosity of less than 20 cSt, and preferably less than 15 cSt. The immiscible liquid may comprise a perfluorocarbon, preferably having a vapor pressure low enough to allow use of the device without exposing the hydrophobic background for 2 or more hours. The method may include using a roughened hydrophobic background, the roughness of the hydrophobic background sufficient to prevent outmigration of immiscible liquid and preferably characterized by an root mean squared roughness of 50-100 micrometers or greater. The roughness of the hydrophobic background, viscosity of the immiscible liquid, surface tension of the background, and surface tension of the immiscible liquid may be chosen so that immiscible liquid remains on the hydrophobic portions of the surface and does not block attachment of the aqueous liquids to the hydrophilic elements. The method may further include performing an assay.

In some embodiments, there is a frame for holding a deformable transparent microfluidic substrate. The frame comprises a plurality of support pillars positioned to hold the substrate in a flat configuration. The pillars are preferably separated by cutout portions.

In some embodiments, the pillars are rounded and/or hydrophobic to reduce the potential for wetting of the pillars. A device may further comprise the substrate, where the substrate optionally has a plurality of spaced apart hydrophilic elements in a hydrophobic background.

In accordance with some embodiments, there is an assay array comprising a deformable microfluidic substrate in a generally planar configuration, a generally rectangular border extending normal to the plane of the substrate, and a supporting grid below the substrate, the substrate preferably having an array of hydrophilic elements in a hydrophobic background and the grid preferably having openings aligned with the hydrophilic elements to permit optical transmission through both the grid and the hydrophilic elements.

In accordance with some embodiments, there is a device for washing a microfluidic array assembly having an array of liquid droplets adhered thereto. The device comprises a mechanism for draining a hydrophobic liquid from the assembly, a mechanism for filling the assembly with an aqueous wash liquid; a mechanism for shaking the assembly in the presence of the aqueous wash liquid; a mechanism for tilting and thereby draining the wash liquid from the assembly; and a spill sensor placed under the assembly to trigger an alarm condition if the spill sensor is contacted by wash liquid.

In accordance with some embodiments, there is a device for washing a microfluidic array assembly having an array of liquid droplets adhered thereto. The device comprises a mechanism for draining a hydrophobic liquid from the assembly, a mechanism for filling the assembly with an aqueous wash liquid; a mechanism for shaking the assembly in the presence of the aqueous wash liquid; a mechanism for tilting and thereby draining the wash liquid from the assembly; an optional spill sensor placed under the assembly to trigger an alarm condition if the spill sensor is contacted by wash liquid; and a reader adapted to read information from the assembly and to use the information to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, to record the date of production of the plate, to record the date of expiry of the plate, and/or to record the number of times the plate has been washed. Optionally, the device includes a writing device for use with a writable identification feature such as an RFID device the writing device operable to store information on the identification feature such as an update to the number of times the plate has been washed.

Some embodiments are implemented as instructions stored in a computer readable storage medium. The instructions may be read and utilized by a computer system in accordance with conventional processes.

BRIEF DESCRIPTION OF THE DRAWINGS

Those skilled in the art should more fully appreciate advantages of various embodiments based on the following "Detailed Description," discussed with reference to the drawings summarized immediately below.

FIG. 1b shows a perspective underside view of the plate/holder assembly of FIG. 1a.

DETAILED DESCRIPTION

Methods and devices described herein allow for effective, efficient and flexible use of patterned fluidic elements. Details of several embodiments are discussed below.

Some embodiments feature or use a patterned hydrophobic/hydrophilic fluidic sample array. In some embodiments, the substrate is flat and has hydrophilic elements that are capable of holding a hydrophilic liquid volume. In some embodiments, the substrate is a glass slide that is patterned with a hydrophobic coating. The hydrophobic coating leaves an array of uncoated regions of glass that act as the hydrophilic elements. The hydrophilic elements may further be coated with hydrophilic coatings to promote specific binding, to discourage nonspecific binding, or both. The held volume is most commonly aqueous, but could also comprise another polar solvent, such as DMSO but, for simplicity, the embodiments refer to aqueous samples. The plate can be a glass plate. The hydrophobic regions can be applied to a glass plate by printing a hydrophobic coating or other suitable method. The hydrophobic regions may be fluorinated or perfluorinated. For example, these may be composed of Teflon® or related material. Optionally, the hydrophilic regions may be coated to increase hydrophilicity, prevent nonspecific binding, present binding probes, or support the adhesion and/or health of cells. Preferably, the hydrophobic regions are arranged on a standard format, such as that for a 96, 384, or 1536 well microplate, or subregion thereof.

As described in U.S. patent application Ser. No. 11/984,197, aqueous samples may be dispensed so that they adhere to the hydrophilic regions. By virtue of its lacking microplate well walls that block transfer of fluid from element to element, the plate may be easily washed by an aliquot or flow of liquid, and excess liquid can easily be drained (e.g., using gravity). A low surface energy liquid may be used to rinse the plate with adhered samples to prevent sample carryover and crosstalk and to cover the adhered samples to prevent evaporation during incubation and analysis. One such fluid is Fluorinert (from 3M). A mixture of perfluoro and hydrofluoro-compounds (bp 180-

230° C.) suitable for this purpose is also available from Curiox Biosystems ("Rinsing Oil"). The system is especially useful for inhomogeneous assays that require binding steps, including cell adhesion, certain nucleic acid assays, and immunoassays. In a preferred embodiment, the surface tension of the hydrophobic coating is less than or equal to the surface tension of the rinsing oil, which is in turn less than the surface tension of the aqueous liquid, which is in turn less than the surface tension of hydrophilic surface.

Figure 1A:
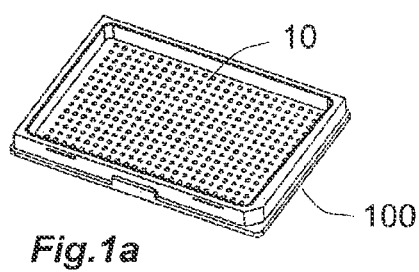
FIG. 1a shows a perspective top view of a plate/holder assembly, in accordance with some embodiments.
Figure 1B:
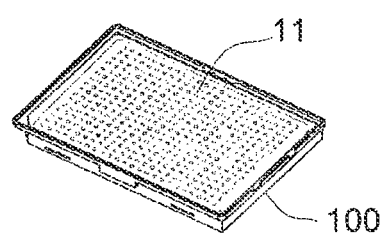
Figure 1C:
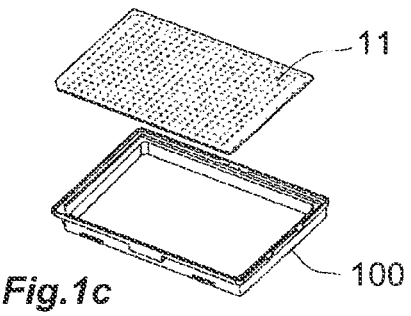
FIG. 1c shows a perspective exploded view of the plate/holder assembly of FIGS. 1a-1b.

FIGS. 1a-1c shows a microfluidic plate assembly 10 having a plate 11 with hydrophilic elements in a hydrophobic background and a plate holder 100. The example shown has 384 elements, in the general format of a microplate. In various embodiments, other formats may be used, including a microscope-slide type format, as described below.

Figure 2A:
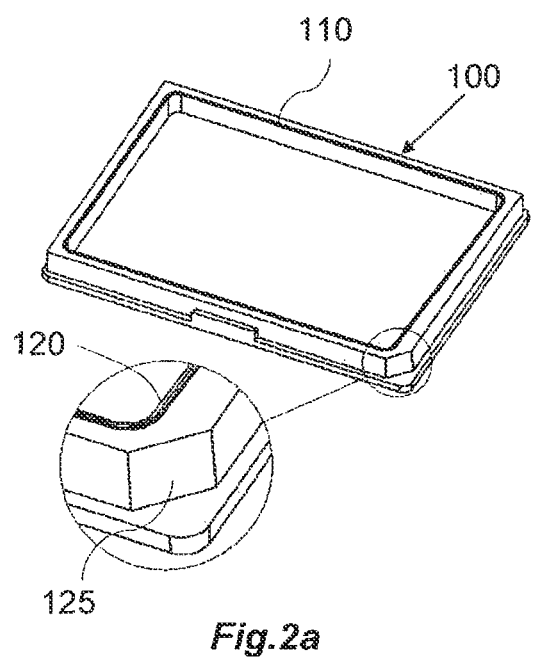
FIG. 2a shows a top perspective view of a plate holder having an upper ridge in accordance with some embodiments.

FIG. 2a shows a top perspective view of a holder 100 that can be used to hold or frame a fluidic plate 11, for ease of manual or automatic handling, in accordance with some embodiments. The plate may have a hydrophobic/hydrophilic pattern as mentioned above, but other microfluidic structures may also benefit from using the holder 100. For low cost, the holder 100 can be made of injection molded plastic, such as polypropylene. The holder 100 can have a generally rectangular shape and can be dimensioned to be compatible with industry standard microplate handling equipment. Alternately, the holder can be dimensioned in a microscope slide format. Other formats are possible. The holder 100 has a circumferential side wall 110. When a plate is mounted in the holder 100, the plate and the wall 110 may form a leak-resistant chamber so that various fluids may be introduced.

In an embodiment, the holder 100 is usable with a cover. The holder 100 may include a raised portion 120, preferably in the form of a rounded bump atop the holder wall 110. An advanced cover design is described below in connection with FIGS. 8-11, but other covers, including simpler designs may be used. The cover may include a resilient gasket that is dimensioned to be complementary to the raised portion 120 so that when the cover is pushed against the holder, a leak-resistant chamber is formed. It is advantageous to place the raised portion toward the inside edge of the side wall 110 to avoid creating a capillary encircling the junction of the side wall 110 and the cover, because the capillary will fill with liquid during use. Optionally, the holder may include a flat corner 125 to act as an orientation reference.

Figure 2B:
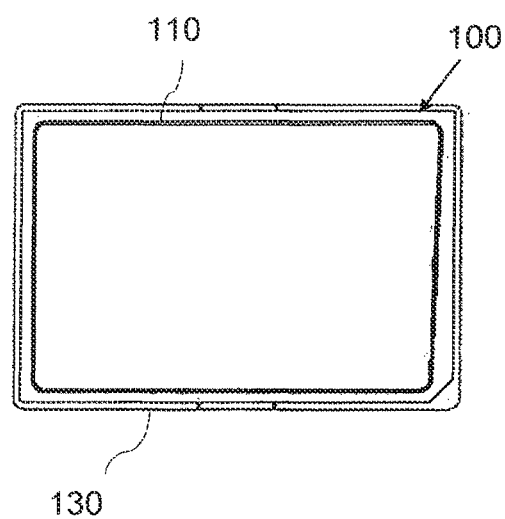
FIG. 2b shows a plan view of a plate holder having a drainage slope, in accordance with some embodiments.

FIG. 2b shows a schematic plan view of the holder 100, in accordance with some embodiments. At least one portion of the side wall 110 forms a slope 130. In use, the holder 100 can at times include a fluidic plate (typically attached to the bottom of the holder 100), with a cover applied (typically to the top of the holder 100), and a liquid held therebetween. For example, the holder/plate will be in this condition when the plate is being washed. The slope 130 is of sufficient angle that when the holder/plate/cover system is tilted from the horizontal (e.g. at 90 degrees) and an outlet is provided near the lowest point of the system, the liquid will drain more effectively than if the holder 100 were perfectly rectangular. In other words, the last drops of draining liquid will flow down the slope and into the drain, thus reducing the residual liquid volume in the system. The slope may be, for example, 1 to 10 degrees, or more. The draining may be passive, using gravity, or active, using suction or centrifugation. The filling and/or draining operations may be performed by an automated instrument.

Figure 3:
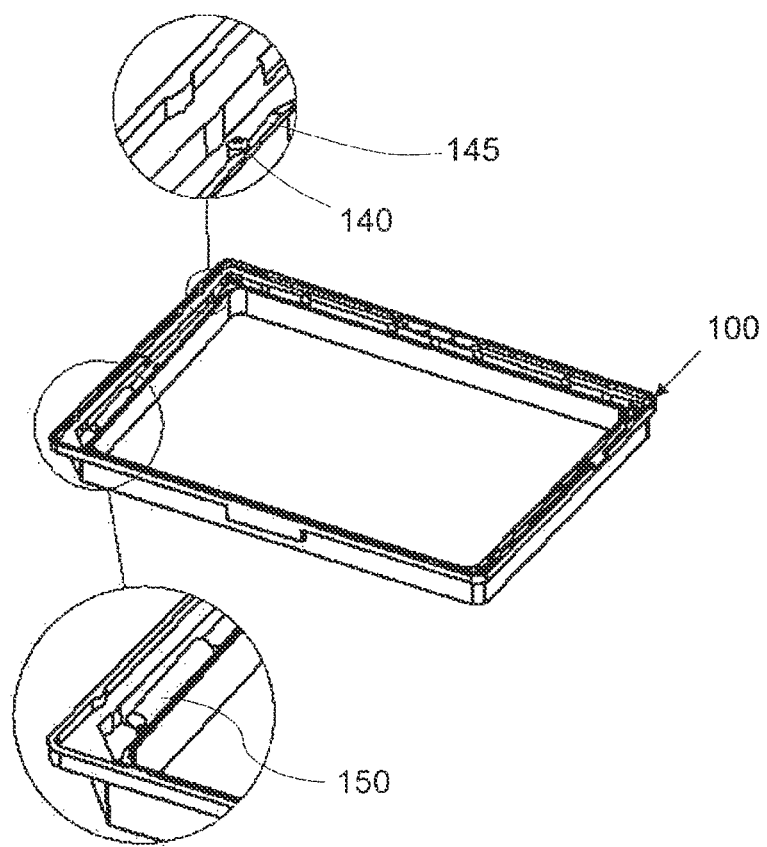
FIG. 3 shows a bottom perspective view of a plate holder having a plate leveling feature and an identification feature in accordance with some embodiments.

FIG. 3 shows a bottom view of the holder 100 having a leveling feature in the form of small feet 140 and a plate identification feature 150. The feet 140 may protrude from a lip 145 and may protrude on the order of, for example, 0.2-0.4 mm. The feet allow for level attachment of a microfluidic plate to the holder 100. By offsetting the plate from a supporting portion of the holder 100, variations in plate high due to the use of a sealant between the plate and the holder 100 are minimized. The sealant may be, for example, and adhesive such as glue or an adhesive tape, or may be an elastomer (in which case the plate can be pressed against the elastomer to for a seal). The use of solid feet 140 causes the plane of attachment of the plate to be determined by the feet rather than the sealant. Preferably, the seal is leakage-resistant. Preferably, the flatness of the plate is 200 micrometers or less in deviation from the average elevation over the area of the plate.

The identification feature is a machine readable identifier such as a bar code or radio frequency tag identity tag (RFID) or other such component. The identifier may also have a write-feature, as in the case of an RFID, which allows a machine to record information thereupon.

When a disposable plate designed for running multiple, specific reactions is introduced to a designated instrument (e.g., a machine for washing the plate), it can be beneficial to identify one or more characteristics of the incoming plate accurately. Such recognition avoids potential confusion in the process, which could lead to wrong information in the end. It is desirable to introduce simple and easy markings and recognize the nature of a plate in order to run a process rightfully programmed for the plate.

At present, many solutions are available for identifying the plate. However, often a recognizing mark such as barcode sticker is introduced by a user during a secondary processing of the plates rather than at the manufacturing stage. Such practice leaves open the possibility of confusing plates made from different manufacturing processes.

The plate holder 100 can have a small pocket along its wall 110, which is used for embedding a REID tag 150. The RFID tag 150 can be used for recording information about the plate, such as the plate type, batch number, date of production, etc. The purpose of RFID (Radio Frequency Identification) is to achieve one or more of the following:

To establish the authenticity of the product used in order to maintain the quality of the results;

To record product information;

To enable automated instrument to extract operational parameters from the RFID and run an optimal process for the particular plate; and To ensure safe operation of the instrument by confirming the presence of a plate in a desired location.

The RFID communication allows for non-contact information exchange established between a RFID tag and a RFID reader or reader/writer. The RFID tag may have its own unique ID. Other than the unique ID, the device can have a readable/writable digital memory (e.g., 1 to 100 bytes or more). The data in the memory may be encoded to include some or all of the following information:

1. Type of the consumable (e.g., 1 for a 384 feature cell analysis plate, 2 for 384-feature ELISA plate, etc.);

2. Date of production;

3. Batch number;

4. Date of Expiry, if any;

5. Operational parameters, such as:

a. type of wash buffer (for instruments that support such choice, otherwise instrument will ignore and use what is available);

b. volume of wash buffer;

c. shaking duration;

d. shaking speed;

e. rest duration before drain;
f. drain duration;
g. 2nd type wash buffer;
h. volume of 2nd wash buffer;
i. 2nd shaking duration;
j. 2nd shaking speed;
k. 2nd rest duration before drain; and
l. 2nd drain duration;

6. number of times used (which is instrument writable data); and

7. A code/algorithm for a washing instrument to establish authenticity.

An RFID reader/writer can be an integrated device in the washing instrument that does one or more of the following:

1. When a consumable product, for example a plate, is placed onto an automated instrument plate handling instrument, the RFID reader can establish the presence of the plate and authenticity of the plate through the code. The confirmation of the presence of the plate is important because the operation of the instrument without the plate in place may result in serious safety breach due to mechanical and electrical hazard, and/or from flooding of liquid reagents in the absence of the plate. RFID communication will avoid the accidental run of the instrument without the plate in place.

2. The RFID reader will check the number of times the consumable is washed. If the number of times washed is more than a specified quantity, the reader will issue a warning to the instrument controller to alert the user.

3. If the instrument has an internal clock, it may compare the expiry date to the current date. If the expiry is reached, it may issue a warning to the instrument controller to alert the user.

4. Upon meeting the conditions as stated above, the reader can extract operational parameters from the REID tag. These parameters will then be sent to the instrument controller, where the controller will use this information to run the operations.

5. Upon the end of a washing operation, the RFID reader, which may also be a writer, of the instrument can update the code for indicating the number of times washed in the RFID tag to indicate that the corresponding plate has been washed one additional time.

6. Upon the end of step 5, the RFID reader will issue an end of operations instruction to the instrument controller to alert the user, or in the case of a fully automated system, the system controller to pick up the consumable.

The detection of a plate by physical contact is particularly useful for running a washing process. A washing instrument is designed to run a washing process when a plate is delivered to the instrument by a user or an automated system. When the plate is not properly positioned on the plate stage (or holder), neither contact sensor is pressed. This may alarm the instrument not to start the washing process. Likewise, when a plate is missing from the instrument by mistake, the washing instrument can be programmed to not start the process, which could otherwise lead to disastrous circumstances. In addition, the differentiation of different plate types is useful by assuring to run a right washing process for the type of a plate introduced. For example, the washing instrument may distinguish between ELISA and cell plates and select an appropriate washing protocol. A user may program to run cell washing process for an ELISA plate or vice versa. In such a case, the washing instrument stops the process and generates an error message before proceeding to the next step.

The RFID recognition method is potentially expensive (although costs are falling). Accordingly, in an alternate embodiment a contact sensor may offer similar advantages by providing a simple, effective solution to prevent the confusion of plates designed for different processes. The plate or plate holder itself is manufactured with a physical key feature such as indented marking or tracking features. The amount of information to be stored in a plate requires different level of tracking feature. For example, to achieve a simple differentiation with four different variables, physical indentation in a plate can be a best method to achieve. If the level of information requires more than 10 different variables, a method like RFID can be employed in order to carry such information.

Figure 4:
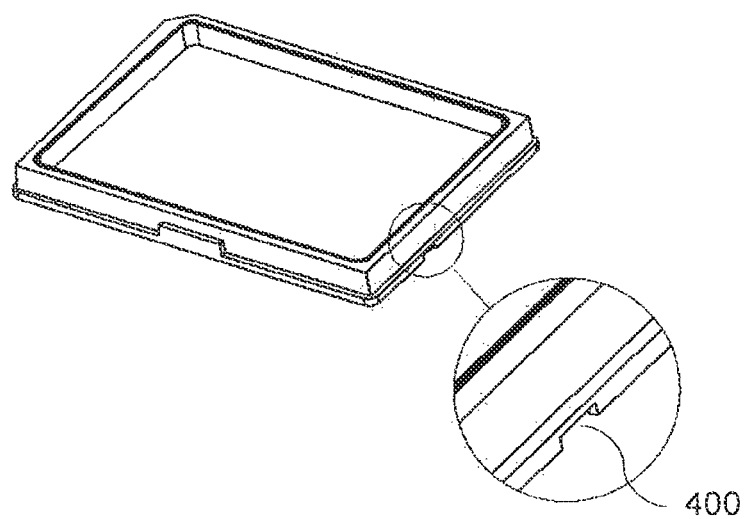
FIG. 4 shows a top perspective view of a plate holder having a physical key feature in accordance with some embodiments.

FIG. 4 shows a plate holder 100 with a physical key-feature. For example, the key-feature may be an indentation our cutout in a plate, which can be recognized by an accepting instrument (e.g., the plate washing instrument described below). One or more cutouts can be made along the edge of the plate holder wall 110 at the size of 2-10 mm. The location of the cutout along the edge is used for making identification of the plate. Two or more cutouts or other features may be used on a single plate, depending on the corresponding receiving platform of a plate washing instrument which may have an array of two or more contact switch/sensors for determination of plate identity.

Figure 5:
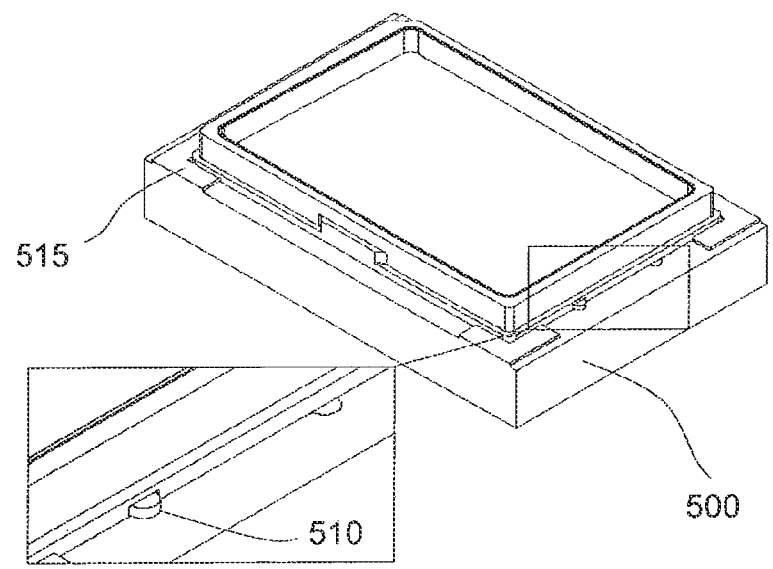
FIG. 5 shows a top perspective view of the plate holder of FIG. 4 mounted on a platform of a washing instrument, in accordance with some embodiments.

FIG. 5 shows the plate loaded onto a receiving platform 500 for certain operations. Alignment features 515 on the platform 500 ensure the plate is placed correctly. The platform has a series of sensors (e.g. switches) 510. Depending on the location of the cutout or cutouts, a different pattern of switches 510 is triggered. A combination of the switch/sensor activation determines the identification of the plate, as well as the state of plate loading action, and determines if a plate is present. If no plate is present, none of the switches/sensors 510 will be activated.

The contact sensors 510 can differentiate, for example, the presence and absence of a plate and ELISA or cell assay type plate when a place is present. If both contact sensors 510 are free, it means that there is no plate. This can prevent accidental triggering of a program when a plate is missing by mistake. The washing instrument that accepts the plate assembly may feature a controller programmed to activate certain operations only when a plate is sensed. For example, when one right sensor is pressed while one left sensor is free, the instrument can perform a washing routine suited for an ELISA plate. When one left sensor 510 is pressed while one right sensor 510 is free, the instrument can perform a washing routine suitable for a cell plate. A fourth option of both sensors 510 pressed can also be used. There can also be more than two switch/sensors 510 along the edge to encode and communicate a greater amount of information about the plates. Although mechanical switches are shown, other types of switches, including optical and electrical switches may be employed.

The detection of a plate by physical contact is particularly useful for running a washing process. A washing instrument is designed to run a washing process when a plate is delivered to the instrument by a user or an automated system. When the plate is not properly positioned on the plate stage (or holder), neither contact sensor 510 is pressed, alarming the instrument not to start the washing process. Likewise, when a plate is missing from the instrument by mistake, the washing instrument will not start the process, thereby preventing potentially adverse circumstances. In addition, the differentiation of an ELISA and a cell plate is useful to assure running the right washing process for the type of a plate introduced. A user may mistakenly program the instrument to run a cell assay washing process for an ELISA plate or vice versa. In such case, the washing instrument can stop the process and generate an error message before proceeding to the next step.

A flat slide attached to a plate holder may become bent. Flatness of the slide at the bottom can be extremely important depending on the usage of the plate. Bending of the bottom slide may happen, particularly when the flat slide is made of a flexible or soft material or is thin. Often, the bending or distortion of the bottom slide leads to a poor quality of optical detection because the flatness is important in obtaining high quality of optical data. The tolerance of the flatness may be less stringent, for example 200 um, for an application such as ELISA, where detection is performed by absorbance or epifluorescence method. In an application for cell imaging or microarray imaging, the tolerance is much tighter, for example less than 50 um.

Figure 6:
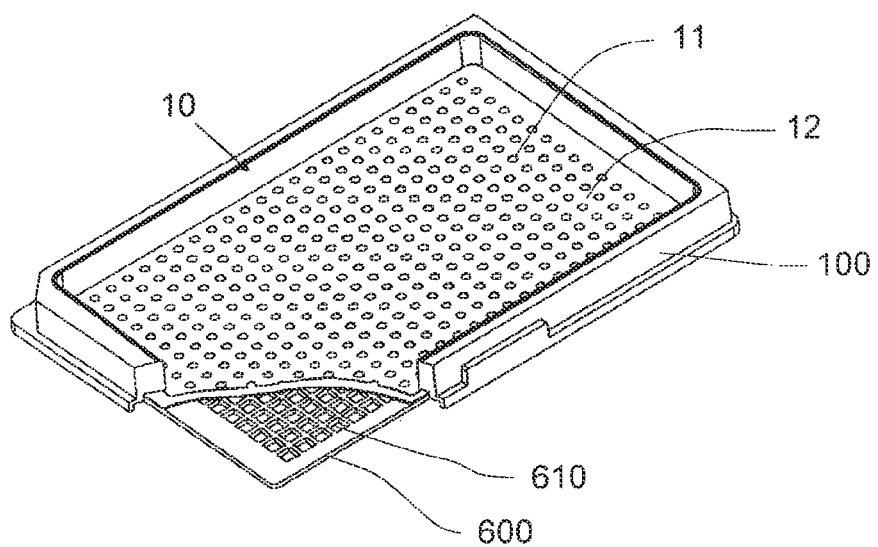
FIG. 6 shows a top perspective view of a plate assembly having an underlying support structure with optical passthroughs, in accordance with some embodiments.

FIG. 6 shows a plate assembly 10 with a flexible plate 11 in a plate holder 100 supported by a support grid 600. The support grid 600 maintains the flatness of the flexible plate. Using the support grid 600 allows the use of plates that are thinner or made of a more flexible material (including polymeric materials) than would otherwise be practical. Holes 610 in the support grid 600 are arranged to be in-line with hydrophilic elements 12 of the plate 11 thus facilitating optical interrogation thereof, especially in transmission-mode. For example, the grid 600 may be thin enough to allow for optical interrogation by a microscope element from below. By positioning the grid 600 below the plate 11, facile washing of the plate is maintained. The size of the holes can be maximized for easier optical access. Preferably, the grid imparts a flatness of the plate is 200 micrometers or less in deviation from the average elevation over the area of the plate.

Figure 7:
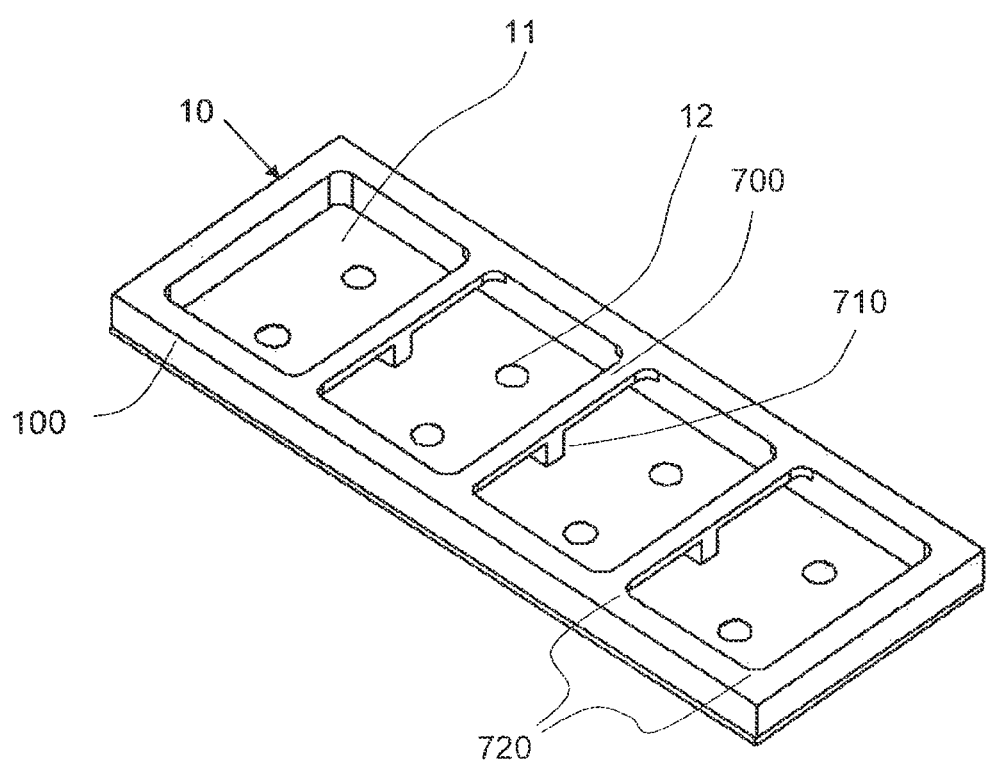
FIG. 7 shows a top perspective view of a plate assembly having an underlying support structure with optical passthroughs and support fingers, in accordance with some embodiments.

FIG. 7 shows another method for supporting a flexible plate using support pillars 710. The pillars 710 support the positioning of a bottom plate 11 (shown here in a microscope slide aspect ratio) but do not interfere with a whole-plate washing of the hydrophilic elements 12. In one example, the plate holder comprises a series of pillars, whose one end contacts a plate 11 and secures the position of the plate 11. In the FIG. 7, the holder 100 contacts the middle of the plate 11 as well as the side of the plate 11. In such manner, the flatness of a plate 11 can be better controlled, particularly when the slide is thin and flexible, for example, a glass slide or plastic slide of thickness 0.17 mm. With the pillars present in the middle of the slide, the surfaces of the pillars may be hydrophobic in order to minimize the wetting of the pillars during exposure to a liquid, in a process such as washing. In addition to the hydrophobic surface property, the pillars can designed to expose round feature instead of edge structure, which is known to help further reduce potential trapping of a liquid or wetting.

The pillars 710 may be disposed on bridges 700, which are disposed between windows 720 that permit optical observation of the elements 12.

In an illustrative embodiment, a bottom slide is a microscope glass slide of 75 mm×25 mm×0.17 mm thickness. For example, the slide holder with pillars has the outer specification of 75 mm×25 mm×5 mm. The holder carries three pillars in the middle of the pocket as shown in FIG. 7. The slide holder is made of, preferably, polypropylene, while the surface, which contacts and bonds to the bottom slide, is treated to become more hydrophilic in order to ensure reasonable bonding of the holder to the slide. The treatment of the surface to become more hydrophilic can be performed by, for example, plasma treatment, which is known to oxidize a polymer surface to become hydrophilic. The size of the pillars is, for example, 1 mm diameter while the bridge holding the pillars is also 1 mm thick with round structure. Preferably, the fingers impart a flatness of the plate that is 200 micrometers or less in deviation from the average elevation over the area of the plate. In an alternate embodiment, the fingers may support the under-side of the plate, or the hydrophilic elements may be on the opposing side.

In various embodiments, the holder 100 may have one or any combination of the raised portion 120, the reference corner 125, the sloped portion 130, leveling features 140, and an identification feature 150, a grid 600, pillars 710, or other features mentioned above.

In accordance with some embodiments, a hydrophobic coating is protected from wetting by a polar liquid (e.g., an aqueous sample). The coating can be created by forming a thin layer of immiscible liquid on top of a solid substrate. In a preferred embodiment, such combination of the solid surface and a thin layer of immiscible liquid satisfies the following conditions: (i) the surface tension of the immiscible liquid is not lower than that of the surface of solid substrate and (ii) the surface tension of the polar liquid is higher than that of the immiscible liquid. For these purposes, a standard solution of phosphate buffered saline may be used as a reference aqueous liquid (137 mM NaCl, 2.7 mM KCl, 10 mM sodium phosphate dibasic, 2 mM potassium phosphate monobasic and a pH of 7.4) to compare surface tensions. In practice, a wide variety of aqueous solutions can be used.

For example, the formation of a thin layer of perfluorocarbon liquid such as perfluorodecane, $CF_3$—$(CF_2)_9$—$CF_3$, on a surface of substrate comprising a perfluorocarbon solid such as polytetrafluoroethylene, produces a coating that is resistant to wetting by many types of aqueous solutions. In this case, the surface tension of the immiscible liquid is similar to that of perfluorocarbon solid. In addition, the surface tension of any aqueous solution is higher than that of the immiscible liquid, satisfying the non-wetting condition presented above.

If the vapor pressure of the immiscible liquid is extremely low, then such coating can be produced on a solid substrate and stored for a long time (e.g., more than 2-48 hours or longer). In fact, the coating may last for 6-12 months or more if the package of the solid substrate is adequately sealed to prevent gas exchange. Furthermore, the thin layer of the immiscible liquid is not washed away completely so long as the liquid is not exposed to perfluoro-based liquid. The liquid stays on the solid surface upon exposure to aqueous and organic liquids as the perfluorocarbon-based liquid is immiscible with neither aqueous nor organic liquid.

The thin layer of the immiscible liquid can be applied to any kind of surface including a surface patterned with hydrophobic and hydrophilic coating (e.g., an array of hydrophilic elements on a hydrophobic background). The hydrophobic part can be protected from wetting as far as the system satisfies the relationship of the surface tensions between the surface, immiscible liquid and sample liquid. The hydrophilic part of the surface, however, is expected to interact with the polar liquid if the surface tension of the immiscible is lower than that of the hydrophilic part. If the thin layer of the immiscible liquid is too thick and/or viscous to recede from the hydrophilic part of the surface, the sample liquid may not be able to interact with the hydrophilic part of the surface. The parameters such as the thickness and viscosity of the immiscible liquid may be adjusted in order to allow the sample liquid to interact with the hydrophilic part of the surface. For example, the thickness of the immiscible liquid can be less than 5 mm, or preferably less than 1 mm. The viscosity (kinematic) of the immiscible liquid can be less than 20 cSt, or preferably less than 15 cSt.

The solid hydrophobic background surface may be rough or roughened to prevent outmigration of the immiscible liquid from the hydrophobic regions to the hydrophilic regions. In a preferred embodiment the root mean squared roughness is at least 10 um or higher, and preferably 50-100 um or greater. The roughness can be a critical parameter because if the hydrophobic area is very smooth, the immiscible liquid may recede from the surface during handling, exposing a dry hydrophobic surface. This leads to the wetting of the dry hydrophobic surface by reagents and solutions in the absence of the immiscible liquid. In an embodiment, the roughness of the hydrophobic background surface, viscosity of the immiscible liquid, and surface tension of the surface and immiscible liquid are chosen so that immiscible liquid remains on the hydrophobic portions of the surface and does not block attachment of aqueous liquids to the hydrophilic elements.

In a specific embodiment, an aqueous solution may be added to one or more array elements after coating with the immiscible liquid and assays may be performed in accordance with the methods of U.S. patent application Ser. No. 11/984,197.

Figure 8:
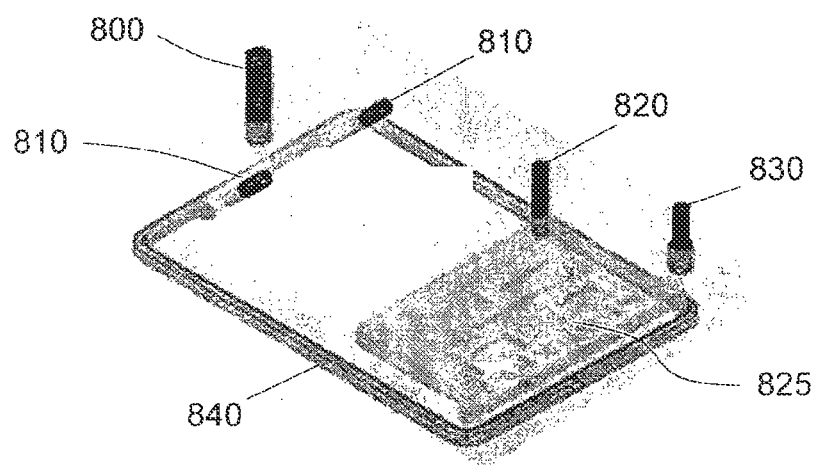
FIG. 8 shows a top perspective view of a cover for a plate assembly, in accordance with some embodiments.
Figure 9:
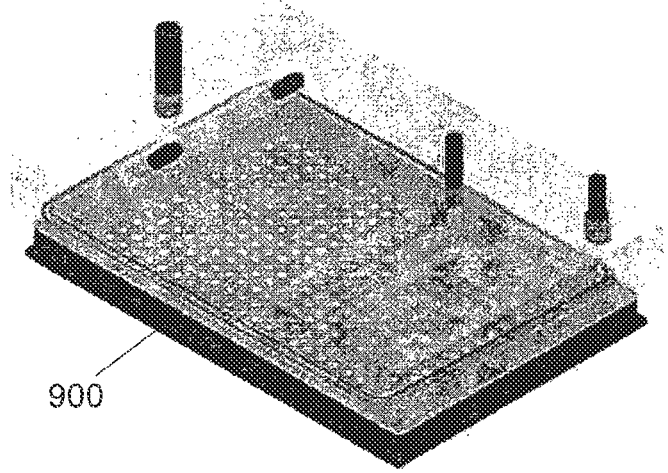
FIG. 9 shows a top perspective view of a covered plate assembly, in accordance with some embodiments.
Figure 10:
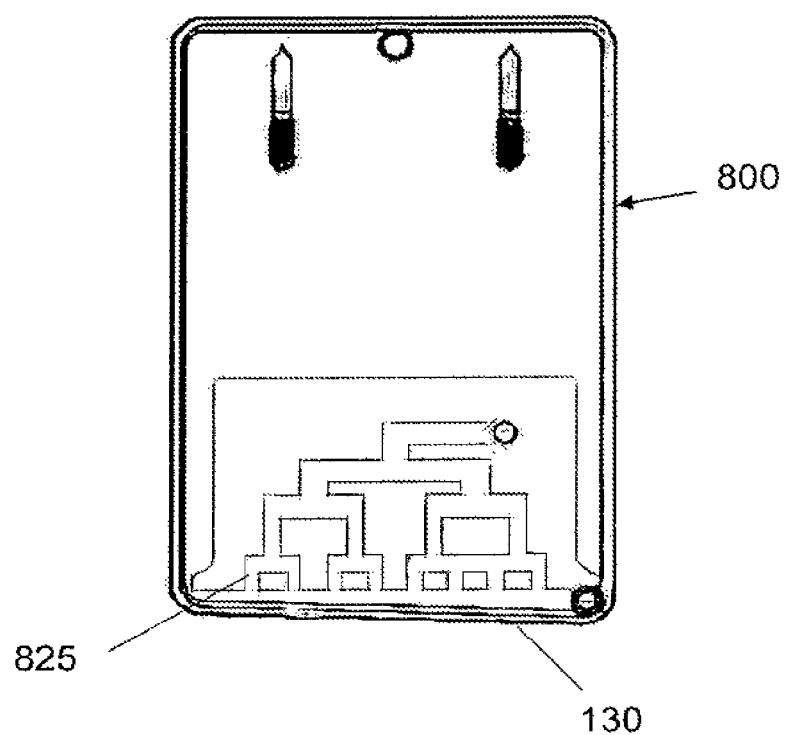
FIG. 10 shows a plan view of a covered plate assembly, in accordance with some embodiments.

FIGS. 8-11 show illustrative embodiments of a cover 800 that is adapted to fit sealingly on plate holder 100. FIG. 8 shows the cover 800 and FIG. 9 shows the cover 800 in an assembly 900 with a plate holder 100 and plate 11. The cover 800 includes several features that may be used individually, or combined in various combinations. An elastomeric gasket 840 is positioned to seal against a raised ridge 120 of the holder 100. As described in herein and in U.S. patent application Ser. No. 11/984,197, hydrophobic immiscible oil may be added to coat the array. The oil may be injected via one or more inlets 810. Angular cutout 811 can be included as an optional design feature. An air vent 800 may be used to prevent unwanted backpressure. The angle of the oil inlet is directed away from the center of the plate so as not to stream oil directly at the hydrophilic elements, which are typically centrally placed. The angle may be chosen to impact the wall 110 of the plate holder 100. In this way, droplets of polar liquid adhered to the elements will not be displaced. The introduction of oil can be made gentler by using multiple oil inlets 800. In a related embodiment, oil can be introduced using a branched structure as described below in connection with a wash buffer.

A wash liquid input system is also provided. Wash liquid (e.g. a buffered aqueous solution) may be introduced via a wash-buffer inlet 820. The wash buffer travels through a branched channel structure 825, which splits the flow of the buffer and introduces the buffer to the chamber formed between the plate 11 and the cover 840. In practice, the assembly 900 may be tilted from the horizontal so that wash buffer is introduced so as to fill the chamber from the bottom up, thereby effecting an even and gentle filling of the chamber. For example, the liquid can be split into 8 streams. Each of the exit channels may, for example, have a width of 1-5 mm, preferably 2-3 mm, with a height of 0.1-0.2 mm, preferably 0.2-1.5 mm, although other configurations are possible. The assembly 900 can be then tilted back to horizontal for shaking, prior to draining.

Figure 11:
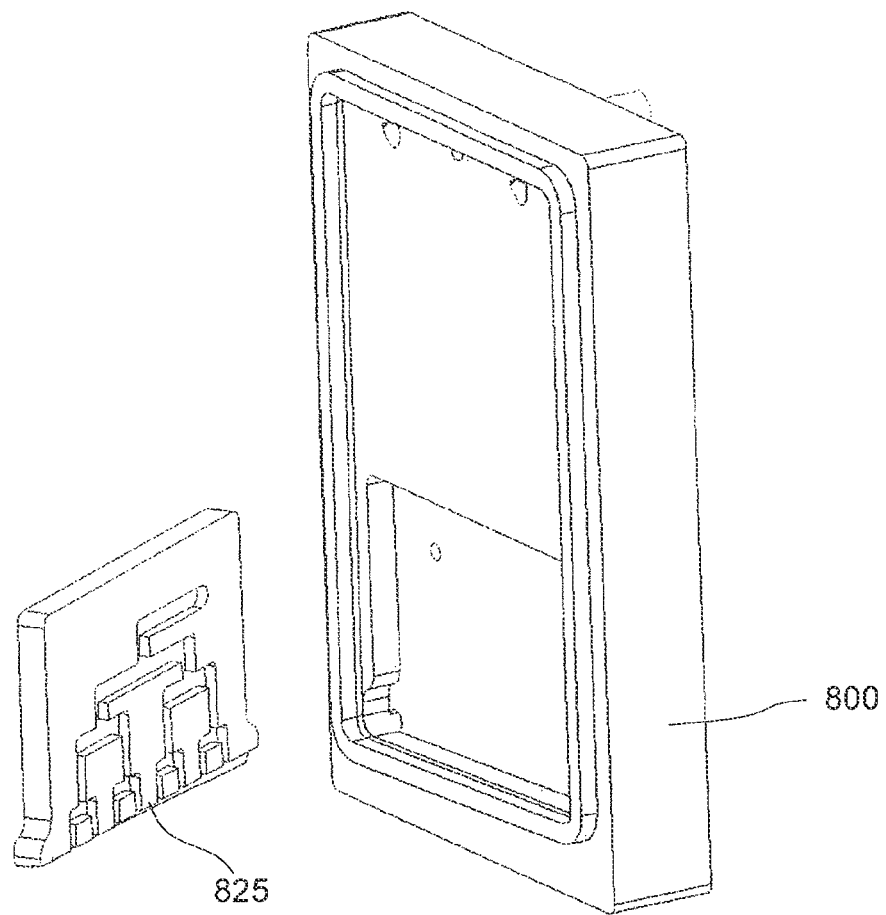
FIG. 11 shows an exploded view of a cover for a plate assembly, in accordance with some embodiments.

FIG. 11 shows a plan view of an embodiment of the assembly 900, further including a sloped portion 130. FIG. 11 shows how the branched channel structure 825 and the rest of the cover 800 may be assembled from 2 pieces.

Figure 12:
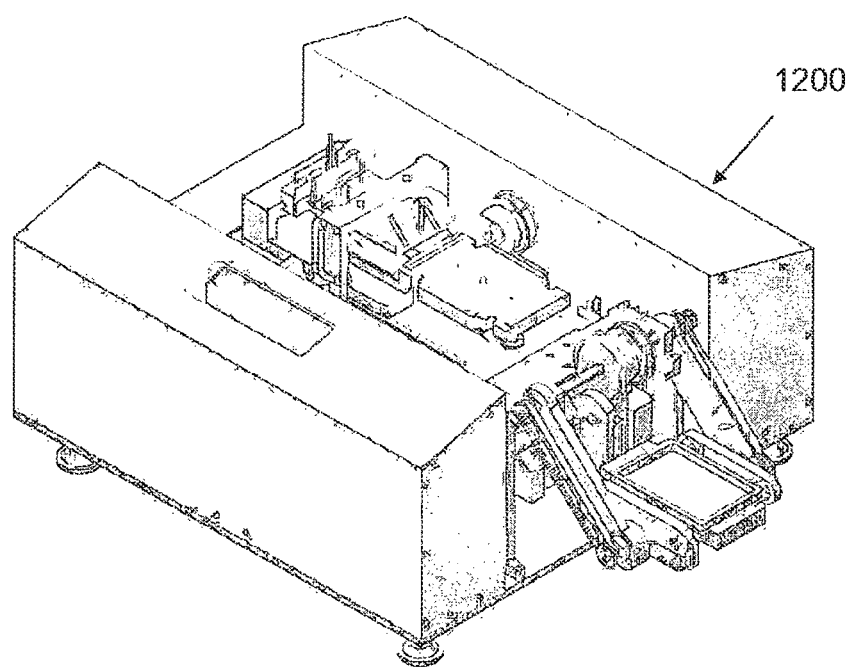
FIG. 12 shows a top perspective view of an instrument for automated plate washing, in accordance with some embodiments.

FIG. 12 shows a top perspective view of a plate washing instrument 1200, in accordance with some embodiments.

The plate washing instrument is designed to wash a plate 11. The washing instrument 1200 can include a mechanism for draining a hydrophobic liquid from a plate assembly 900, a mechanism for filling the assembly with an aqueous wash liquid, a mechanism for shaking the assembly in the presence of the aqueous wash liquid; a mechanism for tilting and thereby draining the wash liquid from the assembly, and a spill sensor placed under the assembly to trigger an alarm condition if the spill sensor is contacted by wash liquid. In addition, the washing instrument 1200 a reader adapted to read information from the assembly and to use the information to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, to record the date of production of the plate, to record the date of expiry of the plate, and/or to record the number of times the plate has been washed, and optionally, a writing device for use with an writable identification feature such as an RFID device the writing device operable to store information on the identification feature such as an update to the number of times the plate has been washed.

Figure 13:
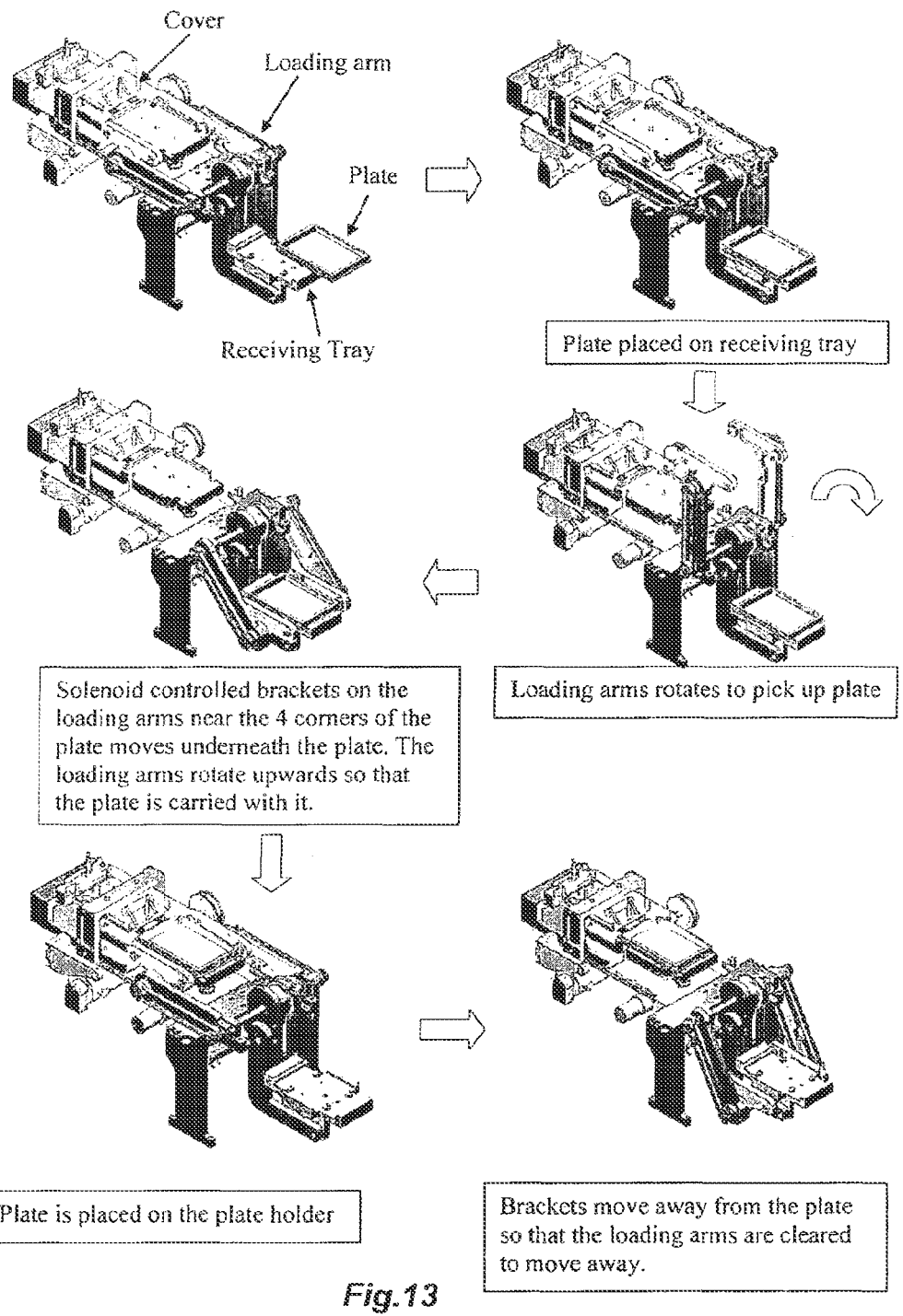
FIG. 13 shows a sequence of operations for loading a plate assembly onto the washing instrument of FIG. 12, in accordance with some embodiments.
Figure 14:
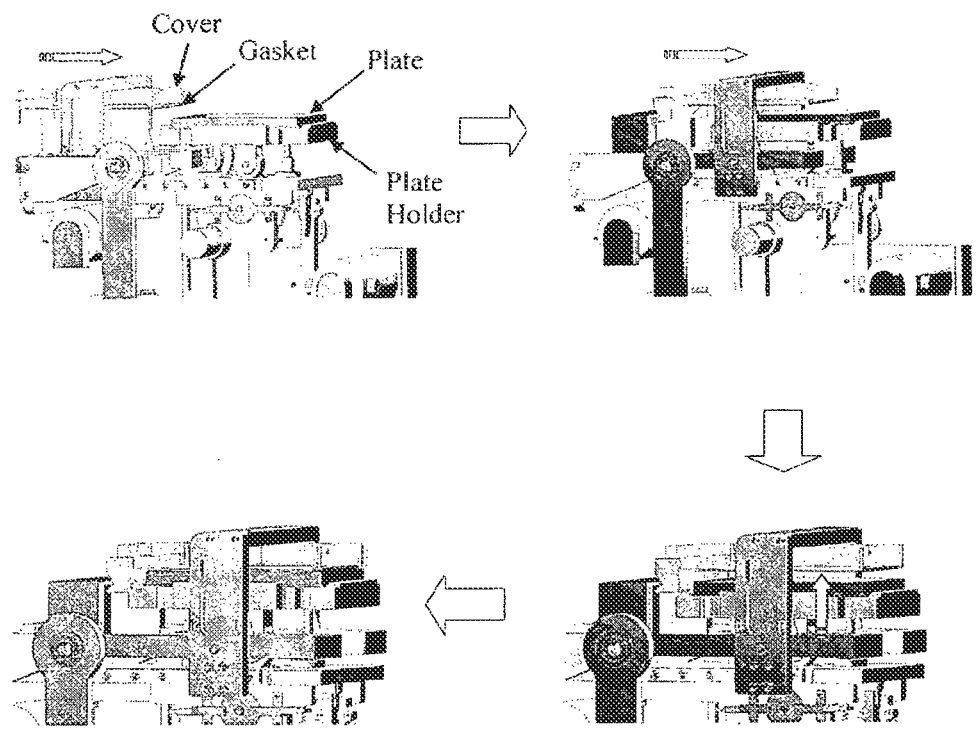
FIG. 14 shows a sequence of operations for covering a plate assembly using the washing instrument of FIG. 12, in accordance with some embodiments.

FIG. 13 shows a sequence of operations of instrument 1200 in loading a plate/holder assembly 10. FIG. 14 shows a sequence of machine operations in which a cover 800 is pressed against a plate/holder assembly 10, to form a covered assembly 900.

Figure 15:
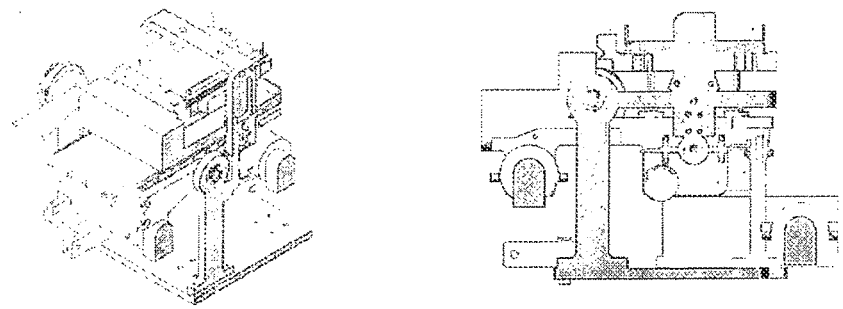
FIG. 15 shows a sequence of operations for tilting the covered plate assembly of FIG. 14 in order to perform fluid exchange operations, in accordance with some embodiments.
Figure 15:
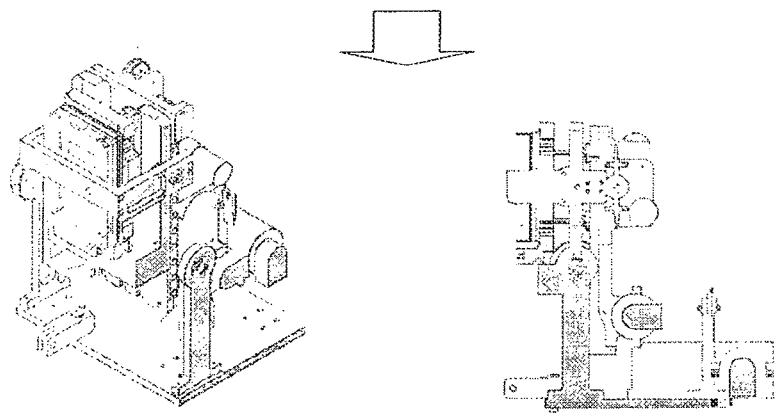
Figure 15:
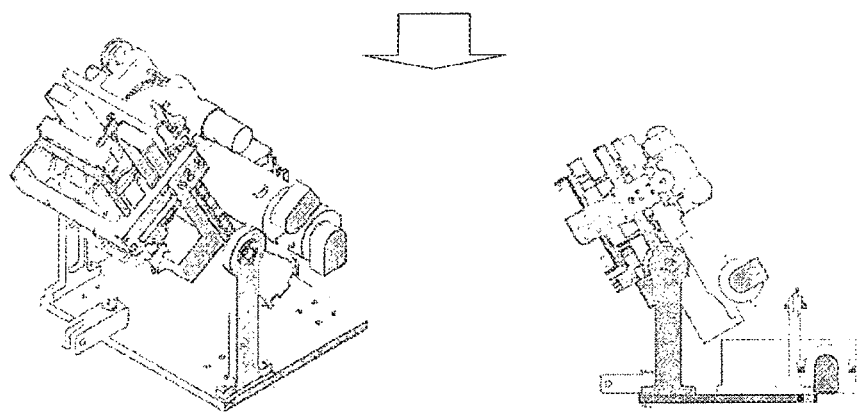

FIG. 15 shows a sequence of machine operations in which the covered assembly 900 is tilted at various angles for addition and removal of immiscible oil and wash buffer, which may be effected automatically using an automated fluid exchange system. In the method of U.S. patent application Ser. No. 11/984,197, the wash buffer was drained at 120 degrees from horizontal. This angle gives effective draining to minimize residual volume. In some embodiments, however, it is realized that for some assay operations, it may be desirable to retain more than a minimal amount of polar liquid on the hydrophilic elements after draining. Accordingly, some embodiments feature a method for controlling a residual volume of an aqueous solution bathing an array comprising a plurality of hydrophilic elements on a hydrophobic background. The method includes adding an aqueous liquid to the array so as to contact the hydrophilic elements and tilting the array to a selected angle from a horizontal reference plane, wherein the angle is less than 120 degrees and preferably between 5 degrees and 115 degrees, (more preferably between 15 and 90 degrees), and allowing the aqueous liquid to drain while leaving a residual volume adhered to the elements. A desired residual volume may be selected and a corresponding angle selected so as to leave behind the desired residual volume. T is may be accomplished by performing calibration experiments to create a lookup table correlating angle to volume. The correlations may also be described by a computational fit to the data (i.e., parameterizing a model equation). For example, using 2 mm diameter hydrophilic regions with adhered PBS buffer, the residual volume after draining approximately correlates to the draining angle as follows:

30 degrees: 0.6-0.8 microliter retained per element;
60 degrees: 0.4-0.6 microliter retained per element; or
90 degrees: 0.2-0.3 microliter retained per element.

Figure 16:
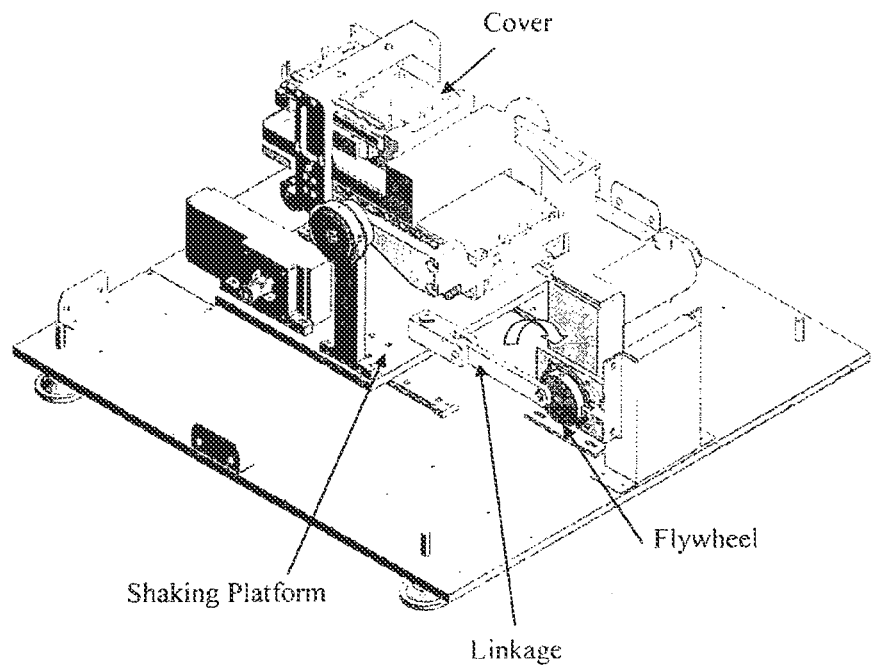
FIG. 16 shows a sequence of operations for shaking the covered plate assembly of FIG. 14, in accordance with some embodiments.
Figure 16:
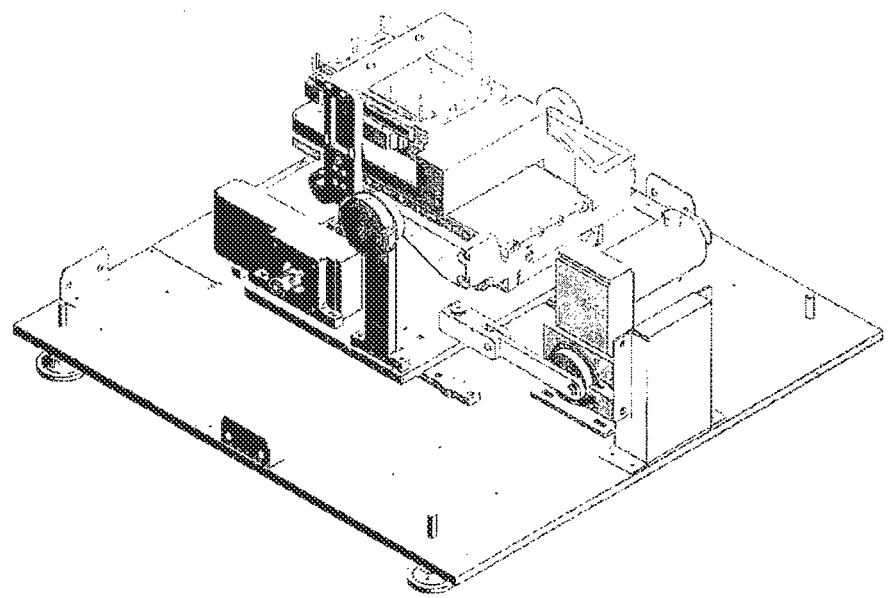

FIG. 16 shows a sequence of operations for shaking the covered assembly 900 in order to wash the hydrophilic elements of the plate 11. A rotating flywheel attached to a linkage imparts an oscillating motion to a shaking platform. The motion causes the wash buffer to splash from side to side, thus creating a washing action.

Figure 17:
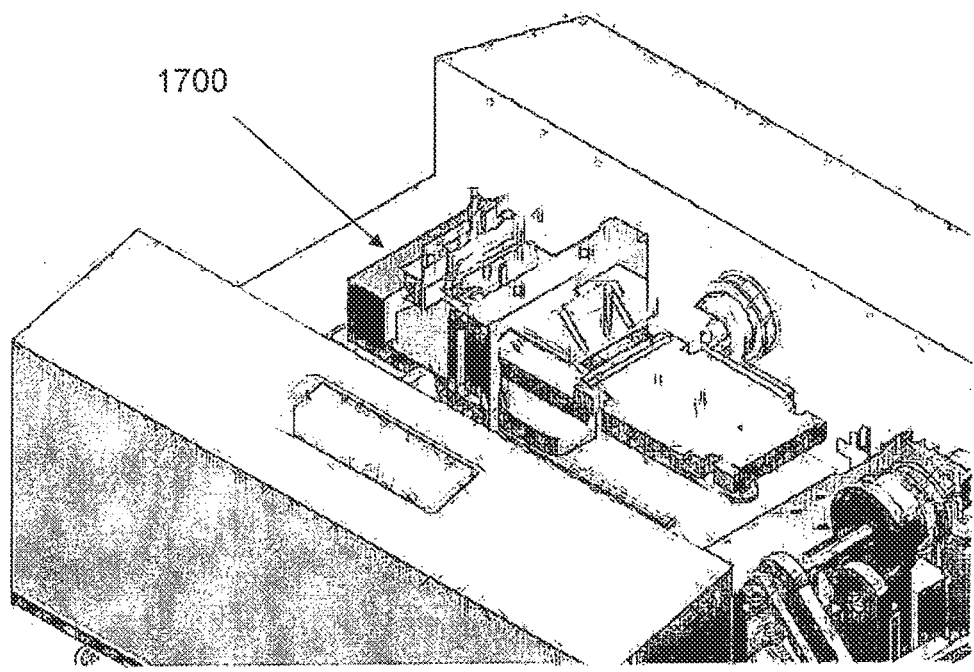
FIG. 17 shows a top perspective view of the instrument of FIG. 12 in which there is a plate holder with RFID antenna and a spill tray.
Figure 18:
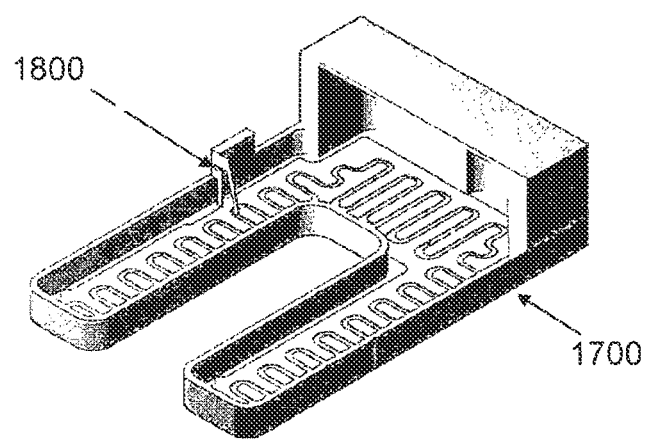
FIG. 18 shows a close-up top perspective view of the spill tray of FIG. 17.
Figure 19:
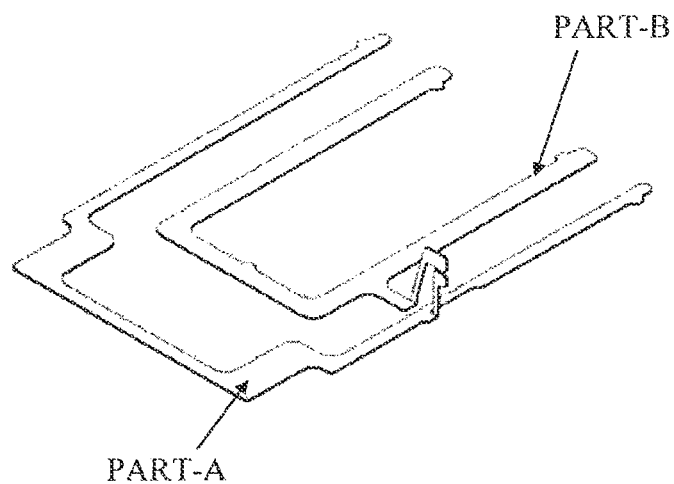
FIG. 19 schematically shows a liquid sensor of the spill tray of FIG. 18.

FIG. 17 shows a safety feature of instrument 1200 in accordance with some embodiments. A spill tray 1700 includes a liquid sensor (e.g. the one shown in FIG. 18). The spill tray 1700 serves two major safety roles in the event of leakage. First, the spill tray 1700 contains majority of the spilled liquid and prevents the liquid leak into the inside of electromechanical section of the instrument. Second, the tray carries two conducting pieces separated by in the range of 1 mm-10 cm, preferably 0.5 cm-3 cm by average. In case of any spillage, a circuit is completed between the two separated pieces, thereby triggering an alarm condition, for example, stopping the ongoing machine operation for manual intervention and repair. FIG. 18 shows an example of a tray 1700 and two separate pieces of electrodes integrated into the tray forming the liquid sensor 1800. The threshold volume of aqueous solution required in order to trigger the alarm may be adjusted by selecting a distance of the electrode; a larger distance will be sensitive only to larger liquid drops. FIG. 19 shows an embodiment of the liquid sensor 1800.

Figure 20:
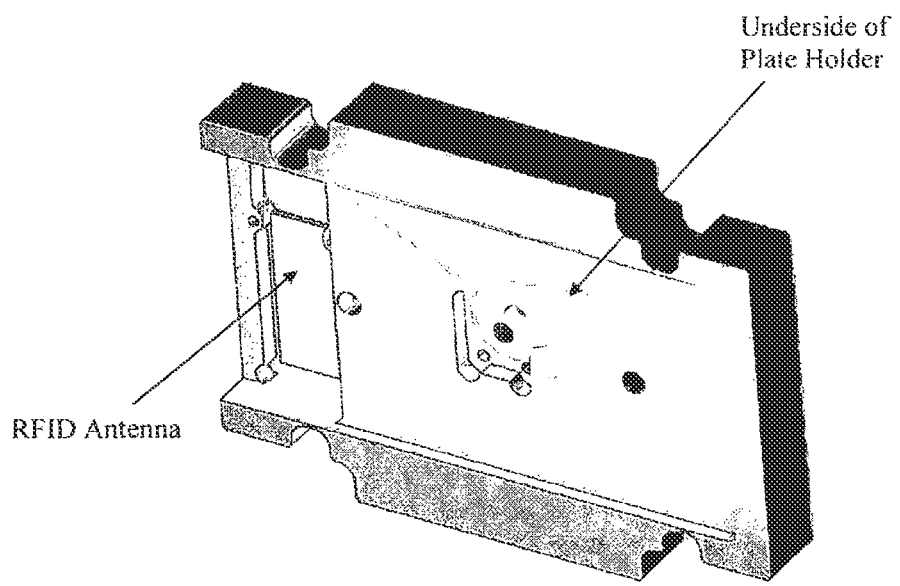
FIG. 20 shows a perspective view of the underside of a plate holder of the instrument of FIG. 12 having an RFID reader.

FIG. 20 shows the underside of a plate holder of an instrument 1200 in accordance with some embodiments. The plate holder is made of a non-conducting material, and has a small pocket to allow a RFID reader/writer antenna to be mounted. The RFID reader/writer antenna is printed on a Printed Circuit Board (PCB). The antenna is connected to a remotely placed RFID reader/writer module by electrical cable. The RFID module, when activated, will detect the presence of a plate with an RFID tag. The detection will act as a safety feature to confirm the plate presence before activating the washing cycle, and also for the purpose of information gathering such as the type of plate or other information described above.

Figure 21:
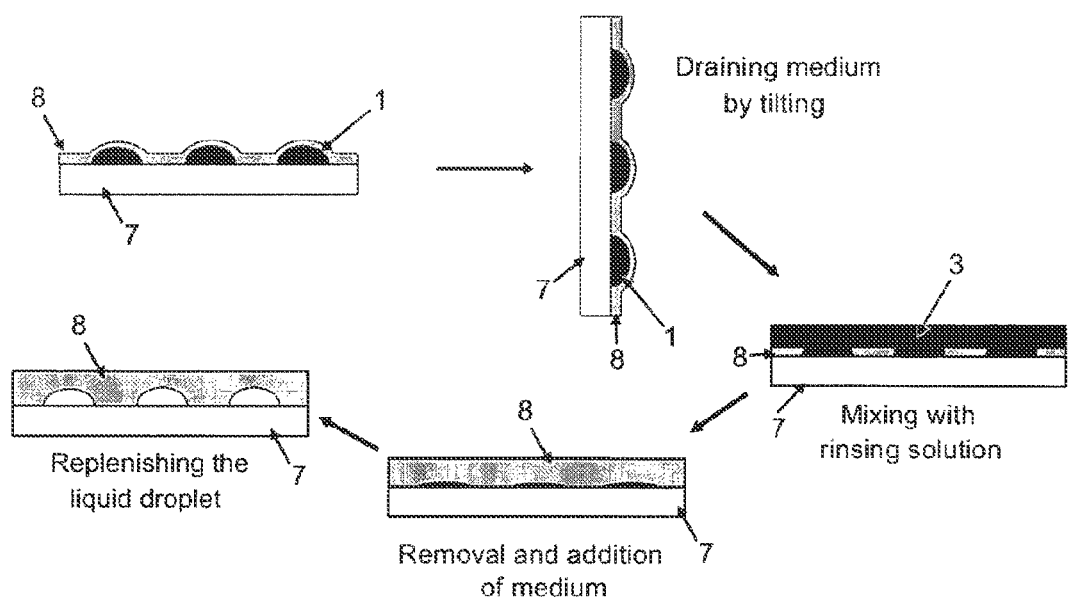
FIG. 21 shows a sequence of washing in accordance with some embodiments.

FIG. 21 depicts a general scheme of rinsing target matter, by using a rinsing solution. A plate 7 with a plurality of liquid droplets 1 thereon is covered with a hydrophobic medium 8 that is immiscible with a liquid of the liquid droplets 1. The plate 7 is tilted, and thereby the hydrophobic medium 8 is drained. In some embodiments, a layer of hydrophobic medium 8 is allowed to remain on the plate 7, thereby covering the hydrophobic surface thereof. Droplets left on the surface may likewise be covered by a thin layer of hydrophobic medium 8. Thereafter the plate is immersed in or exposed to a rinsing solution 3, such that the contents of all liquid droplets are rinsed. Upon removal from the rinsing solution 3, a layer of rinsing solution may be allowed to remain on the plate 7 thereby covering the hydrophilic area(s) on its surface as a thin film. The plate 7 is immersed in a hydrophobic medium 8 again or a hydrophobic medium is applied to the plate 7. Finally, liquid droplets are replenished on each hydrophilic area by depositing a hydrophilic liquid on the hydrophilic areas of the plate 7.

In some embodiments, a washing or rinsing process includes using a medium, which is immiscible with a liquid of a liquid droplet (e.g. a hydrophobic medium). In some embodiments, the medium is removed before rinsing the liquid droplet to form a thin layer of the medium, or exchanged with a thin fluid medium. The respective thin fluid medium is immiscible with the liquid of the liquid droplet. Furthermore, the thin fluid medium is of a lower surface energy than the liquid of the liquid droplet. As an illustrative example, the thin fluid medium may be of higher hydrophobicity than the liquid of the liquid droplet. In some embodiments, the medium that is immiscible with the liquid of the liquid droplet and the thin fluid medium are miscible. In some embodiments, the thin fluid medium is of a lower viscosity than the medium that has been disposed into the apparatus. This may be desired to facilitate the rinsing process. As an illustrative example, the viscosity of the thin fluid medium may be below about 40 centistoke, such as below about 20 centistoke. In some embodiments the boiling point of the thin fluid medium is selected in the range between about 25° C. and about 600° C., such as between about 40° C. and about 400° C.

In some embodiments, washing or rinsing includes tilting the plate. In some embodiments, the plate is tilted before rinsing/washing the liquid droplet. Thereby the medium, which is immiscible with the liquid of the liquid droplet, or the thin fluid medium is allowed to at least essentially drain from the plate. Furthermore, the liquid droplet remains immobilized on the hydrophilic surface area of the plate. In some embodiments, a layer, such as a film, of the medium that is immiscible with the liquid of the liquid droplet (e.g. hydrophobic medium, or thin fluid medium) is allowed to remain on the plate, as depicted in FIG. 21.

In some embodiments, the disclosed methods for instrument control and assay are implemented as a computer program product for use with a computer system. For example, a control system for an embodiment of the above described washing instrument may be sold as a computer program product for use with an existing washing instrument. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments, the principles described herein may be implemented as a combination of both software (e.g., a computer program product) and hardware. Still some embodiments are implemented as entirely hardware, or entirely software.

Although the above discussion discloses various exemplary embodiments, it should be apparent that those skilled in the art can make various modifications that will achieve some of the advantages of the principles described herein without departing from the true scope of the principles described herein.

What is claimed is:

1. A device for washing an array plate, comprising:
a holder adapted to hold an array plate having an array of liquid droplets thereon;
a wash liquid input system adapted to provide an aqueous wash liquid over the array plate when the array plate is mounted in the holder, wherein the wash liquid input system includes a fluid-exchange cover with one or more inlets, the fluid-exchange cover adapted to come into contact with the array plate and sealingly cover the array plate along the contact between the fluid-exchange cover and the array plate and adapted to allow the aqueous wash liquid to be provided through the one or more inlets of the fluid-exchange cover over the array plate when the array plate is mounted in the holder;
a shaker mechanically coupled with the holder and adapted to shake the array plate in presence of the aqueous wash liquid when the array plate is mounted in the holder; and
a rotation arm mechanically coupled with the holder and the fluid-exchange cover and adapted to tilt the array plate and remove the aqueous wash liquid from the array plate when the array plate is mounted in the holder.

2. The device of claim 1, wherein:
the array of liquid droplets is covered with a hydrophobic medium immiscible with the array of liquid droplets; and
the rotation arm is adapted to tilt the array plate and drain the hydrophobic medium from the array plate when the array plate is mounted in the holder.

3. The device of claim 1, further comprising:
a spill sensor placed under the holder to trigger an alarm condition if the spill sensor is contacted by the aqueous wash liquid.

4. The device of claim 1, further comprising:
a reader adapted to read identification information from the array plate when the array plate is mounted;
memory storing operational information associated with the identification information; and
a controller adapted to determine whether the array plate is mounted on the device at a predetermined location in response to receiving the identification information from the reader, authenticate the array plate based on the memory storing the operational information associated with the identification information, control a washing process by setting one or more parameters based on the operational information associated with the identification information, identify a number and/or an arrangement of hydrophilic features on the array plate based on the operational information associated with the identification information, and retrieve a number of times the array plate has been washed, update the number of times the array plate has been washed based on the one or more parameters set for the washing process, and record an updated number of times the array plate has been washed.

5. The device of claim 4, wherein the one or more parameters are selected from a group consisting of: a type of the aqueous wash liquid, a volume of the aqueous wash liquid, a duration of shaking, a speed of shaking, a rest duration before draining the aqueous wash liquid, a duration for draining the aqueous wash liquid, a tilt angle for draining the aqueous wash liquid.

6. The device of claim 5, wherein the controller is configured to control initiation of multiple washing steps by sequentially initiating operations of the wash liquid input system, the shaker, and the rotation arm.

7. The device of claim 6, wherein the one or more parameters include one or more of: a type of a second aqueous wash liquid, a volume of the second aqueous wash liquid, a duration of second shaking, a speed of second shaking, a rest duration before draining the second aqueous wash liquid, a duration for draining the second aqueous wash liquid, a tilt angle for draining the second aqueous wash liquid.

8. The device of claim 1, further comprising:
a writing device for use with a writable identification feature paired with the array plate when the array plate is mounted in the holder, the writing device operable to store in the writable identification feature information including a number of times the array plate has been washed.

9. The device of claim 1, further comprising:
a mechanism for providing the hydrophobic medium to the array plate, when the array plate is mounted in the holder, subsequent to removing the aqueous wash liquid from the array plate.

10. A method for washing an array plate, the method comprising:
mounting, in a holder, an array plate having an array of liquid droplets thereon;
causing a fluid-exchange cover with one or more inlets to come into contact with the array plate and sealingly covering the array plate with the fluid-exchange cover along the contact between the fluid-exchange cover and the array plate;
providing, through the one or more inlets of the fluid-exchange cover, an aqueous wash liquid over the array plate;
shaking the array plate in presence of the aqueous wash liquid; and
tilting the array plate and removing the aqueous wash liquid from the array plate.

11. The method of claim 10, wherein:
the array of liquid droplets is covered with a hydrophobic medium immiscible with the array of liquid droplets; and
the method includes draining the hydrophobic medium from the array plate by tilting the array plate.

12. The method of claim 11, wherein draining the hydrophobic medium from the array plate includes maintaining a layer of the hydrophobic medium that extends over, and covers, the array of liquid droplets.

13. The method of claim 11, further comprising, subsequent to draining the aqueous wash liquid from the array plate, providing the hydrophobic medium to cover the array of liquid droplets.

14. The method of claim 11, wherein the aqueous wash liquid is provided after the hydrophobic medium is drained.

15. The method of claim 10, further comprising:
detecting a spillage of the aqueous wash liquid using a spill sensor placed under the array plate and configured to trigger an alarm condition if the spill sensor is contacted by the aqueous wash liquid.

16. The method of claim 10, including:
placing the array plate in a device for washing the array plate, wherein the device includes:

the holder adapted to hold an array plate having an array of liquid droplets thereon;

a wash liquid input system adapted to provide the aqueous wash liquid over the array plate when the array plate is mounted in the holder, wherein the wash liquid input system includes the fluid-exchange cover with an input channel for receiving the aqueous wash liquid and one or more output channels for outputting the aqueous wash liquid toward the array plate when the array plate is mounted in the holder;

a shaker mechanically coupled with the holder and adapted to shake the array plate in a presence of the aqueous wash liquid when the array plate is mounted in the holder; and a rotation arm mechanically coupled with the holder and adapted to tilt the array plate and remove the aqueous wash liquid from the array plate when the array plate is mounted in the holder; and initiating operation of the device.

17. The method of claim 16, wherein the device also includes a controller, and the method further includes:

using the controller to configure one or more parameters of the device, wherein the one or more parameters are selected from a group consisting of: a type of the aqueous wash liquid, a volume of the aqueous wash liquid, a duration of shaking, a speed of shaking, a rest duration before draining the aqueous wash liquid, a duration for draining the aqueous wash liquid, a tilt angle for draining the aqueous wash liquid.

18. The method of claim 16, wherein the device is configured to sequentially initiate operations of the wash liquid input system, the shaker, and the rotation arm.

19. The method of claim 18, wherein the one or more parameters include one or more of: a type of a second aqueous wash liquid, a volume of the second aqueous wash liquid, a duration of second shaking, a speed of second shaking, a rest duration before draining the second aqueous wash liquid, a duration for draining the second aqueous wash liquid, a tilt angle for draining the second aqueous wash liquid.

20. The method of claim 19, further comprising:

storing in a writable identification feature paired with the array plate information including a number of times the array plate has been washed.

21. The method of claim 10, wherein providing the aqueous wash liquid over the array plate includes providing the aqueous wash liquid so that the aqueous wash liquid contacts multiple liquid droplets of the array of liquid droplets.

22. The device of claim 1, wherein the fluid-exchange cover includes a washing liquid input channel in communication with a branched channel structure that divides the flow of the aqueous wash liquid injected into the input channel into a plurality of output channels so that the aqueous wash liquid from the plurality of output channels is provided over the array plate when the array plate is mounted in the holder.

23. The device of claim 1, wherein:

the wash liquid input system is adapted to provide the aqueous wash liquid through the one or more inlets while the array plate, mounted in the holder, is tilted and sealingly covered by the fluid-exchange cover.

* * * * *